US007666590B2

(12) United States Patent
Cogburn et al.

(10) Patent No.: US 7,666,590 B2
(45) Date of Patent: Feb. 23, 2010

(54) IDENTIFICATION OF FAT AND LEAN PHENOTYPES IN CHICKENS USING MOLECULAR MARKERS

(75) Inventors: Larry A. Cogburn, New London, PA (US); Wilfrid G. Carre, Edinburgh (GB); Xiaofei Wang, Nashville, TN (US)

(73) Assignee: University of Delaware, Newark, DE (US)

( * ) Notice: Subject to any disclaimer, the term of this patent is extended or adjusted under 35 U.S.C. 154(b) by 555 days.

(21) Appl. No.: 11/013,546

(22) Filed: Dec. 16, 2004

(65) Prior Publication Data
US 2005/0214814 A1  Sep. 29, 2005

Related U.S. Application Data

(60) Provisional application No. 60/530,051, filed on Dec. 16, 2003.

(51) Int. Cl.
 C12Q 1/68 (2006.01)
 C12P 19/34 (2006.01)
 C07H 21/04 (2006.01)
(52) U.S. Cl. .......................... 435/6; 435/91.2; 536/23.1
(58) Field of Classification Search ........................ None
 See application file for complete search history.

(56) References Cited

OTHER PUBLICATIONS

Davidson S 'Research suggests importance of haplotypes over SNPs.' Nat Biotechnol. Nov. 2000;18(11):1134-5.*
Juppner H 'Functional properties of the PTH/PTHrP receptor.' Bone. Aug. 1995;17(2 Suppl):39S-42S.*
Hacker UT et al 'Lack of association between an interleukin-1 receptor antagonist gene polymorphism and ulcerative colitis.' Gut. May 1997;40(5):623-7.*
Wang X et al 'Duplicated Spot 14 genes in the chicken: characterization and identification of polymorphisms associated with abdominal fat traits.' Gene. May 12, 2004;332:79-88.*
Cao ZP et al 'Association of Spot14alpha gene polymorphisms with body weight in the chicken.' Poult Sci. Sep. 2007;86(9):1873-80.*
Thisted RA 'What is a P-value?' 1998, from www.stat.uchicago.edu/~thisted, pp. 1-6.*
Griffin, H.D.; Goddard, C., "Rapidly growing broiler (meat-type) chickens: their origin and use for comparative studies of the regulation of growth," Int. J. Biochem; 1994; vol. 26, No. 1; pp. 19-28.
Abasht, Benham et al.; "Fatness QTL on Chickent Chromosome 5 and Interaction with Sex," Genet. Sel. Evol.; 2006; vol. 38; pp. 297-311.
Beccavn, C. et al.; "Insulin-like growth factors and body growth in chickens divergently selected for high or low growth rate," Journal of Endocrinology; 2001; vol. 168; pp. 297-3065.
Boardman Paul E. et al.; "A Comprehensive Collection of Chickens cDNAs," Current Biology; Nov. 19, 2002; vol. 12; pp. 1965-19696.
Brown, Suzanne B., et al.; ""Spot 14" Protein Functions at the Pretranslational Level in the Regulation of Hepatic Metabolism by Thyroid Hormone and Glucose," The Journal of Biological Chemistry, Jan. 24, 1997 Issue, vol. 272, No. 4, pp. 2163-2166.
Carre, W. et al.; "Development of 112 unique expressed sequence tags from chicken liver using an arbitrarily primed reverse transcriptase-polymerase chain reaction and single strand conformation gel purification method," Animal Genetics; 2001; vol. 32; pp. 289-297.
Clarke et al.; "Nutritional Control of Rat Liver Fatty Acid Synthase and S14 mRNA Abundance," The Journal of Nutrition; 1990; vol. 120; pp. 218-224.
Cogburn, Larry A., et al., "Expressed Sequence Tags, DNA Chip Technology and Gene Expression Profiling," Poultry Genetics, Breeding and Biotechnology; 2003; pp. 629-646.
Cogburn, L.A. et al.; "Systems-wide Chicken DNA Microarrays, Gene Expression Profiling, and Discovery of Functional Genes," Poultry Science; 2003; vol. 82; pp. 939-951.
Cogburn et al.; "DNA Microarray analysis of gene expression in liver of broiler chickens divergently selected for growth rate," Poultry Science; 2000; 72 (suppl. 1); p. 72.
Compe, Emmanuel, et al.; "Spot 14 Protein Interacts and Co-operates with Chicken Ovalbumin Upstream Promoter-Transcription Factor 1 in the Transcription of the L-Type Pyruvate Kinase Gene Through a Specificity Protein 1 (SP1) Binding Site," Biochem. J., 2001, No. 358, pp. 175-183.
Conway, Greg; "A novel gene expressed during zebrafish gastrulation identified by differential RNA display," Mechanisms of Development; 1995; vol. 52; pp. 383-391.
Cunningham, Barbara A., et al.; "Spot 14 Protein-Protein Interactions: Evidence for Both Homo-and Heterodimer Formation in Vivo," Endocrinology; 1997; vol. 138, No. 12; pp. 5184-5188.
Cunningham, Barbara A., et al.; "Spot 14 Protein: A Metabolic Integrator in Normal and Neoplastic Cells," Thyroid, 1998, vol. 8, No. 9; pp. 815-825.
Deeb, N., et al., "Genetic Architecture of Growth and Body Compositsions in Unique Chicken Populations," The American Genetic Association; 2002; vol. 93; pp. 107-118.
de Genova Gaya, Leila, et al.; "Genetic Trends of Abdominal Fat Content in a Male Broiler Chicken Line," Genetics and Molecular Research, 2005, vol. 4; pp. 760-764.
Falconer, et al.; "Introduction to Quantitative Genetics," Longmans Green, Harlow, Essex, U.K.; 1996; Chapter 7; pp. 108-121.
Griffin, Harry D. et al.; "Adipose Tissue Lipogeneis and Fat Deposition in Leaner Broiler Chickens," The Journal of Nutrition; 1992; vol. 122; pp. 363-368.
Grillasca, Joel-Paul et al.; "Cloning and initial characterization of human and mouse Spot 14 genes," FEBS Letters; 1997; vol. 401; pp. 38-42.
Hacker, U. T., et al., "Lack of Association Between an Interleukin-1 Receptor Antagonist Gene Polymorphism and Ulcerative Colitis," GUT, May 1997, vol. 40, pp. 623-627.

(Continued)

Primary Examiner—Stephen Kapushoc
(74) Attorney, Agent, or Firm—RatnerPrestia

(57) ABSTRACT

The present invention provides methods of screening chickens to determine those more likely to have a lean or fat phenotype. The invention also provides methods of screening chickens to identify a polymorphism associated with a fat or lean phenotype.

5 Claims, 7 Drawing Sheets

OTHER PUBLICATIONS

Havenstein, G. B., et al.; "Carcass Composition and Yield of 1957 Versus 2001 Broilers When Fed Representative 1957 and 2001 Broiler Diets," Poultry Science, 2003, vol. 82; pp. 1509-1518.

Huang, Xiaoqiu, et al., "CAP3: A DNA Sequence Assembly Program," Genome Res.; 1999; vol. 9; pp. 868-877.

Ikeobi, C.O.N. et al.; "Quantitative trait loci affecting fatness in the chicken," Animal Genetics; 2002; vol. 33; pp. 428-435.

Jump, Donald B. et al.; "Rapid Effects fo Triiodothyronine on Hepatic Gene Expression," The Journal of Biological Chemistry; Mar. 10, 1984; vol. 259, No. 4; pp. 2789-2797.

Jump, Donald B., et al., "High Basal Expression and 3,5,3'-Triiodothyronine Regulation of Messenger Ribonucleic Acid $_{s14}$ in Lipogenic Tissues," Endocrinology; 1985; vol. 117; pp. 2259-2266.

Jump, Donald B. et al.; "Polyunsaturated fatty acids inhibit S14 gene transcription in rat liver and cultured hepatocytes," Proc. Natl. Acad. Sci.; Sep. 1993; vol. 40; pp. 8454-8458.

Jump, Donald B. et al.; "Coordinate regulation of glycolytic and lipogenic gene expression by polyunsaturated fatty acids," Journal of Lipid Research; 1994; vol. 35; pp. 1076-1084.

Jump, Donald B., et al., "Functional Interaction between Sterol Regulatory Element-binding Protein-1c, Nuclear Factor Y, and 3,5,3'-Triiodothyronine Nuclear Receptors," The Journal of Biological Chemistry; Sep. 14, 2001; vol. 276, No. 37; pp. 34419-34427.

Jüppner, H., "Functional Properties of the PTH/PTHrP Receptor," Bone, 1995, vol. 12, No. 2; Supplement; pp. 39S-42S.

Kaiser, et al.; "Microsatellite Polymorphism Between and Within Broiler Populations," Poultry Science; 2000, vol. 79, pp. 626-628.

Kinlaw, William B. et al.; "Direct Evidence for a Role of the "Spot 14" Protein in the Regulation of Lipid Synthesis," The Journal of Biological Chemistry; Jul. 14, 1995; vol. 270, No. 28; pp. 16615-16618.

Koo, Seung-Hoi and Towle, Howard C.; "Glucose Regulation of Mouse $S_{14}$ Gene Expression in Hepatocytes," The Journal of Biological Chemistry; Feb. 18, 2000; vol. 275, No. 7; pp. 5200-5207.

Lagarrigue, Sandrine et al.; "An initial QTL Scan for Abdominal Fatness and Breast Muscle Weight in Broiler Chickens," Plant & Animal Genomes XI Conference; Jan. 11-15, 2003, San Diego, CA.

Leclercq, B., Blum, J.C. and Boyer, J.P.; "Selecting Broilers for Low or High Abdominal Fat: Initial Observations," British Poultry Science; 1980; vol. 21; pp. 107-113.

Legrand, Philippe and Hermier, Dominique; "Hepatic Δ9 desaturation and plasma VLDL level in genetically lean and fat chickens," International Journal of Obesity; 1992; vol. 16; pp. 289-294.

Liaw, Chen W and Towle, Howard C.; "Characterization of a Thyroid Hormone-responsive Gene from Rat," The Journal of Biological Chemistry; Jun. 10, 1984; vol. 259, No. 11; pp. 7253-7260.

Liu, Hsien-Ching and Towle, Howard C.; "Functional Synergism between Multiple Thyroid Hormone Response Elements Regulates Hepatic Expression of the Rat $S_{14}$ Gene," Molecular Endocrinology; 1994; vol. 8; pp. 1021-1037.

Moncur et al.; "The Spot 14 gene resides on the telomeric end of the 11q13 amplicon and is expressed in lipogenic breast cancers: Imlications for control of tumor metabolism," Proc. Natl. Acad. Sci; Jun. 1998; vol. 95; pp. 6989-6994.

O'Hea, E.K. and Leveille, G.A.; "Lipogenesis in Isolated Adipose Tissue of the Domestic Chick (*Gallus domesticus*)," Comp. Biochem. Physiol.; 1968; vol. 26; pp. 111-120.

Seelig, Steven et al.; "Thyroid hormone attenuates and augments hepatic gene expression at a pretranslational level," Proc. Notl. Acad. Sci.; Aug. 19841; vol. 78, No. 8; pp. 4733-4737.

Tatusov, Roman L., Koonin, Eugene V., Lipman, David J.; "A Genomic Perspective on Protein Families," Science; Oct. 24, 1997; vol. 278; pp. 631-637.

Thisted, Ronald A., "What is a P-value?," The University of Chicago, Departments of Statistics and Health Studies, May 1998; pp. 1-6.

Wang, Xiaofei, et al., "Duplicated Spot 14 Genes in the Chicken: Characterization and Identification of Polymorphisms Associated with Abdominal Fat Traits," Gene, 2004, vol. 332; pp. 78-88.

Whitehead, C.C. and Griffin, H.D.; "Development of Divergent Lines of Lean and Fat Broilers using Plasma Very Low Density Lipoprotein Concentration as Selection Criterion: The First Three Generations," British Poultry Science; Oct. 1984; vol. 25, No. 4; pp. 573-582.

Zerehdaran, S., et al.; "Estimation of Genetic Parameters for Fat Deposition and Carcass Traits in Broilers," Poultry Science Association, Inc., 2004, vol. 83; pp. 521-525.

Zhang, Peng, Gu, Zhenglong, Li, Wen-Hsiung; "Different evolutionary patterns between young duplicate genes in the human genome," Genome Biology; 2003; vol. 4, No. 9, Article R56; pp. R56.1-R56.6.

Zhou, H., Lamont, S.J.; "Genetic characterization of biodiversity in highly inbred chicken lines by microsatellite markers," Animal Genetics; 1999; vol. 30; pp. 256-264.

Zhu et al.; "Spot 14 Gene Deletion Increases Hepatic de Novo Lipogenesis," Endocrinology; Oct. 2001; vol. 142, No. 10; pp. 4363-4370.

Campbell, et al., "Human Spot 14 Glucose and Thyroid Hormone Response: Characterization and Thyroid Hormone Response Element Identification," *Endocrinology*, 144(12):5242-5248.

\* cited by examiner

Figure 1

A. THRSPα

```
                                     32F
gaggagaggcaaggagtggggccATGGAGCAGTACTTCTCGGCCACGCAGAAGATGGAGCAGGAGGTGATGTTCCCCAGC
                       M  E  Q  Y  F  S  A  T  Q  K  M  E  Q  E  V  M  F  P  S
 93R
CTGCTGCGAGGGGTCTTCCCGCAGGACGGGGCCGACCCAGCCACCGGCGGCCCCGCAGACCTCTACGAGCACTACCAGCT
 L  L  R  G  V  F  P  Q  D  G  A  D  P  A  T  G  G  P  A  D  L  Y  E  H  Y  Q  L
                                           DeletionF
CCTCAAGGCCATCAAGCCCGTGGTGGAGCGAGGCCTGGCCTCCGTCACCGATCAGAGCCCCACCAGCAATGCCGACGCCG
 L  K  A  I  K  P  V  V  E  R  G  L  A  S  V  T  D  Q  S  P  T  S  N  A  D  A  D ACACGGCCCCATATGATGGCATAGATGGCATAGATGGGAATCTGGAGGAGCGGCTGTCCCACCACATGAATGGCTTGCAG
 T  A  P  Y  D  G  I  D  G  I  D  G  N  L  E  E  R  L  S  H  H  M  N  G  L  Q
DeletionR
CAGGTTCTGACCGACCTCACCAAAAACACCAAAGCTCTCACCCGGAGGTACAGCCAGATCCTGGAGGAGATCAACCTCGG
 Q  V  L  T  D  L  T  K  N  T  K  A  L  T  R  R  Y  S  Q  I  L  E  E  I  N  L  G
                                            ▼
TGAAGGTCAGAGCAGCTCATGAGCCTGCACACGGAGACTCCAagggtgatctgacgtttgcagcccagcggcagctttat
 E  G  Q  S  S  S  *
tcctgtgccaagtcccaccaaggaatgtcttctgcacagaccagcacagaggcttggctgtaccatccaagctgccacat
ggccaatcctcccggcaaacctcactgctttgtttcacctccattcccggggattgccttgcagtaggcagggcagaaat
gagcgttcgctgttattgcttcctagaaggcatctgtaaccttgaaacaatgcttttgttctgcatgtgcctagaccacc
tccccactagtttctttgataatgtcaccagttcccaaagtcaatgatctgaaataaaatgcaataataaaatgaaaaaa
aaaactcagtgcggaatttgaaa
```

B. THRSPβ

```
                                    32F
gcgaggcgaagcgcggggccATGGAGCGGTACTTCTCGGCCACGCAGAAGATGGAGCAGGAGGTGATGTTCCCCAGCC
                    M  E  R  Y  F  S  A  T  Q  K  M  E  Q  E  V  M  F  P  S  L
 93R                                                                 138F
TGCTGCGAGGGGTCTTCCCGCAGGACGGGGCCGACCCAGCCGCCGACGGCCCCGCGGACCTCTACGAGCGCTACCAGC
 L  R  G  V  F  P  Q  D  G  A  D  P  A  A  D  G  P  A  D  L  Y  E  R  Y  Q  L
                                 ParalF
TCCTCAAGGCCATCAAGCCCGTGGTGGAGCGAGGCCTGGCGTCCTTCACCGAGCGCAGCTCCGCCGGCCACGCCGACG
 L  K  A  I  K  P  V  V  E  R  G  L  A  S  F  T  E  R  S  S  A  G  H  A  D  A CCGACGCCGACGCCGAGGACGCGGCGGCCGCAGCCGACGGGGCGGCCGGCAGCCTGGAGCAGCGGCTGTGCCACCACC
 D  A  D  A  E  D  A  A  A  A  D  G  A  A  G  S  L  E  Q  R  L  C  H  H  L
         ParalR                        361R
TGGCCGGGCTGCAGCAGATCCTCAGCCACCTGACCAGGGACACCGCCGCCCTGACGCGCCGCTACAGCCAGATCCTGG
 A  G  L  Q  Q  I  L  S  H  L  T  R  D  T  A  A  L  T  R  R  Y  S  Q  I  L  E AGCGGATCAGCCCCGGCGACGCGCAGCCCAGCTGGTGACCCCGCGCGGCTCCGCTCAGCGCCGCGGGACGGGGCGGCC
 R  I  S  P  G  D  A  Q  P  S  W  *

TCCGAGCGGCGCCGGCAGAGCCGCGGAGCCGTCTGCGGGGCCGTCCCGCGGTGCCCCGCGGCTCCGCCGTGCGCTCCG
TCCTCGGAGAGCGCCGCGCTGCCGCGCTGGGCTCGGACGGAGCCGTGCGGCGCCGGCGCCTTCGGGCTGGATCCCGGA
GCCGCGCAGCGCTGCCCTCTCTCGTGTTTTCTAATAAAACTCGTGTTTTTCCGCAAAAAA
```

Figure 2

```
cTHRSPα         ----------------MEQYFSATQKMEQEVMFPSLLRGVFPQD--------------------
cTHRSPβ         ----------------MERYFSATQKMEQEVMFPSLLRGVFPQD--------------------
hTHRSP          --MQVLTKRYPKNCLLTVMDRHAAEVHNMEQVVMEPSLLRDVQLSG--------------------
mTHRSP          --MQVLTKRYPKNCLLTVMDRYSAVVRNMEQVVMEPSLLRDVQLSG--------------------
rTHRSP          --MQVLTKRYPKNCLLKVMDRYSAVVRNMEQVVMEPSLLRDVELMG--------------------
zTC194742       -MMQICDSYNQKNSLFNAMNREIGAVNNMDQTVMVPSLLRDVPLDQ--------------------
zG12            --MQMSEPLSQKNALYTAMNRELGAVNNMDQTVMVPSLLRDVPLDQ--------------------
zTC192887       MMQLSNDSHCNKHSLLNVMNREIAAANNMDETIMVPNLLRDVPLED-------------------Q
hSTRAIT11499    -MMQICDTYNQKHSLFNAMNREIGAVNNMDQTVMVPSLLRDVPLAD---PGLDNDVGVEVGGSGGC
mSTRAIT11499    -MMQICDTYNQKHSLFNAMNREIGAVNNMDQTVMVPSLLRDVPLSE---PEID-EVSVEVGGSGGC
cSTRAIT11499    --MQICDSYSQKYSLFNAMNREIGAVNNMDQTVMVPSLLRDVPLLGELD----------------- cTHRSPα         -------------GADPATGGPADLYEHYQLLKAIKPVVERGLASVTDQSPTSNADADTAPYDG--
cTHRSPβ         -------------GADPAADGPADLYERYQLLKAIKPVVERGLASFTERSSAGHADADADAEDAAA
hTHRSP          -------------PGGQAQAEAPDLYTYFTMLKAICVDVDHGLLPREEWQAKVAGSE----ENGTA
mTHRSP          -------------PGGSVQDGAPDLYTYFTMLKSICVEVDHGLLPREEWQAKVAGNETSEAENDAA
rTHRSP          -------------YGGSVQDGAPDLYTYFTMLKSICVEVDHGLLPREEWQAKVAGNEGSEAENEAA
zTC194742       ---EEEKEVTSFQDG--------DLYGSIVLLKSIRNDIEWGVLQ--------AEERRKEKHGVTT
zG12            ---EKEQQKLTNDPGSYLREAEADLYSYYSQLKSIRNNLEWGVIR--------SEDQRRKKD--TS
zTC192887       ESHASVSHNNNNNNEPSFPNKQRDLYEHYLLLKSIKNDMEWGILKREMAGGASFLEMAVKQEELPQ
hSTRAIT11499    LEERTPPVPDSGSANGSFFAPSRDLYSHYVLLKSIRNDIEWGVLHQPPPPAGSEEGSAWKSKDILV
mSTRAIT11499    LEERTTPAPSPGSANESFFAPSRDLYSHYVLLKSIRNDIEWGVLHQPSSPPAGSEESTWKPKDILV
cSTRAIT11499    --AAGAVCPEREAAPGGAYFSRRDLYSHYVLLKSIRNDIEWGVQQAAGEEAARKKDKLG------ cTHRSPα         -IDGIDG-------NLEERLSHHMNGLQQVLDLTKNTKAITREYSQILEEINLGEGQSSS
cTHRSPβ         AADGAAG-------SLEQRLCHHLAGLQQILSHLTRDTAALTREYSQILERISPGDAQPSW
hTHRSP          ETEEVEDESASGELDLEAQFHLHFSSLHHILMILTEKAQEVTREYQEMTGQVW--------
mTHRSP          ETEEAEEDRISEELDLEAQFHLHFCSLHHIPHLTRKAQEVTREYQEMTGQVL--------
rTHRSP          ETEEAEEDRLSEELDLEAQFHLHFSSLHHILTLTQKAQEVTQRYQEMTGQVL--------
zTC194742       TSLEVSR-IEPNDKDLEKLFHYHLSGLHTVLAKLTRKANTLTNRYKQEIGIGGCGN-----
zG12            ASEPVRT-EEESDMDLEQLLQFHLKGLHGVLSQLTSQANNLTNRYKQEIGISGWGQ-----
zTC192887       MKGEAVE-EGP---DLEGQFHYHLHGLFSVLSKLTVQADHLTNRYKREIGGGSLLR-----
hSTRAIT11499    DLGHLEG-ADAGEEDLEQQFHYHLRGLHTVLSKLTRKANILTNRYKQEIGFGNWGH-----
mSTRAIT11499    GLSHLES-ADAGEEDLEQQFHYHLRGLHTVLSKLTRKANILTNRYKQEIGFSNWGH-----
cSTRAIT11499    --GGPAE-EAEAEEDLEQQFHYHLSGLHTVLSKLTRKANVLTNRYKQEIGFGSWGQ-----
```

Figure 4
A.
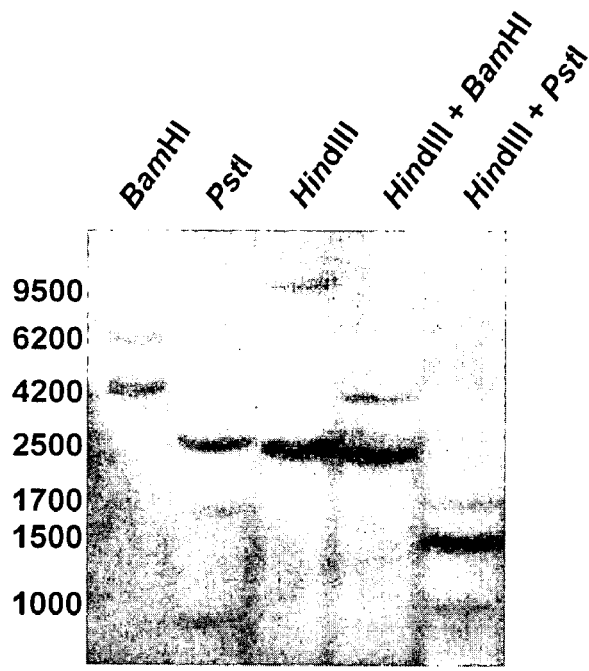
B.
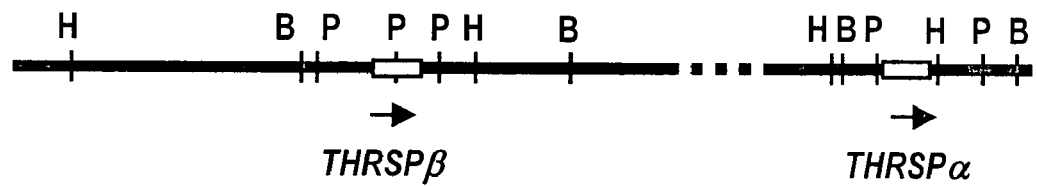
C. *THRSPα*
THRSP
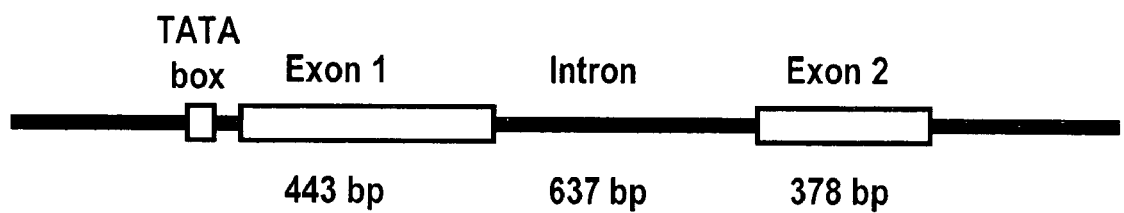

Figure 6
A.
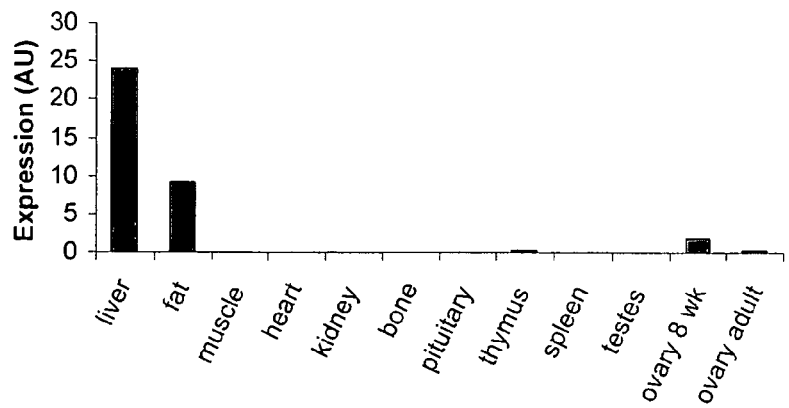
B.
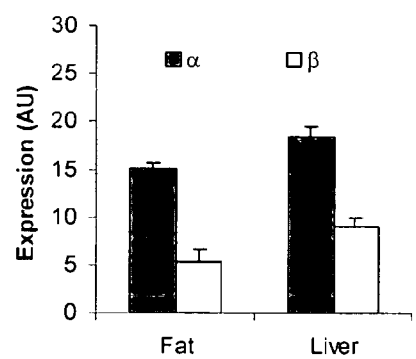
C.
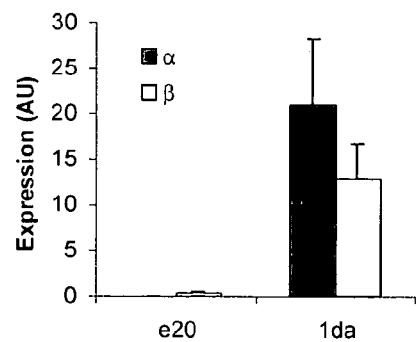
D.
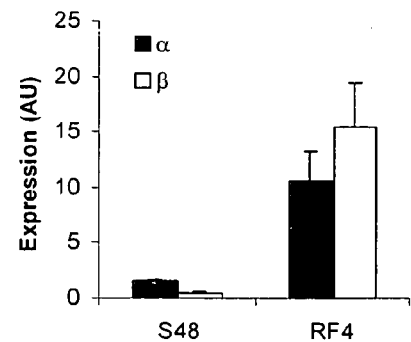

SEQUENCE LISTING

<160> NUMBER OF SEQ ID NOS: 25

<210> SEQ ID NO 1
<211> LENGTH: 823

```
<212> TYPE: DNA
<213> ORGANISM: Gallus gallus

<400> SEQUENCE: 1
gaggagaggc aaggagtggg gccatggagc agtacttctc ggccacgcag aagatggagc    60
aggaggtgat gttccccagc ctgctgcgag gggtcttccc gcaggacggg gccgacccag   120
ccaccggcgg ccccgcagac ctctacgagc actaccagct cctcaaggcc atcaagcccg   180
tggtggagcg aggcctggcc tccgtcaccg atcagagccc caccagcaat gccgacgccg   240
acacggcccc atatgatggc atagatggca tagatgggaa tctggaggag cggctgtccc   300
accacatgaa tggcttgcag caggttctga ccgacctcac caaaaacacc aaagctctca   360
cccggaggta cagccagatc ctggaggaga tcaacctcgg tgaaggtcag agcagctcat   420
gagcctgcac acggagactc caagggtgat ctgacgtttg cagcccagcg gcagctttat   480
tcctgtgcca gtcccacca aggaatgtct tctgcacaga ccagcacaga ggcttggctg   540
taccatccaa gctgccacat ggccaatcct cccggcaaac ctcactgctt tgtttcacct   600
ccattcccgg ggattgcctt gcagtaggca gggcagaaat gagcgttcgc tgttattgct   660
tcctagaagg catctgtaac cttgaaacaa tgcttttgtt ctgcatgtgc ctagaccacc   720
tccccactag tttctttgat aatgtcacca gttcccaaag tcaatgatct gaaataaaat   780
gcaataataa aatgaaaaaa aaaactcagt gcggaatttg aaa                     823

<210> SEQ ID NO 2
<211> LENGTH: 132
<212> TYPE: PRT
<213> ORGANISM: Gallus gallus

<400> SEQUENCE: 2

Met Glu Gln Tyr Phe Ser Ala Thr Gln Lys Met Glu Gln Glu Val Met
1               5                   10                  15

Phe Pro Ser Leu Leu Arg Gly Val Phe Pro Gln Asp Gly Ala Asp Pro
            20                  25                  30

Ala Thr Gly Gly Pro Ala Asp Leu Tyr Glu His Tyr Gln Leu Leu Lys
        35                  40                  45

Ala Ile Lys Pro Val Val Glu Arg Gly Leu Ala Ser Val Thr Asp Gln
    50                  55                  60

Ser Pro Thr Ser Asn Ala Asp Ala Asp Thr Ala Pro Tyr Asp Gly Ile
65                  70                  75                  80

Asp Gly Ile Asp Gly Asn Leu Glu Glu Arg Leu Ser His His Met Asn
                85                  90                  95

Gly Leu Gln Gln Val Leu Thr Asp Leu Thr Lys Asn Thr Lys Ala Leu
            100                 105                 110

Thr Arg Arg Tyr Ser Gln Ile Leu Glu Glu Ile Asn Leu Gly Glu Gly
        115                 120                 125

Gln Ser Ser Ser
    130

<210> SEQ ID NO 3
<211> LENGTH: 684
<212> TYPE: DNA
<213> ORGANISM: Gallus gallus

<400> SEQUENCE: 3
gcgaggcgaa gcgcgggacc atggagcggt acttctcggc cacgcagaag atggagcagg    60
aggtgatgtt ccccagcctg ctgcgagggg tcttcccgca ggacggggcc gacccagccg   120
```

```
ccgacggccc cgcggacctc tacgagcgct accagctcct caaggccatc aagcccgtgg    180
tggagcgagg cctggcgtcc ttcaccgagc gcagctccgc cggccacgcc gacgccgacg    240
ccgacgccga ggacgcggcg gccgcagccg acggggcggc cggcagcctg agcagcggc     300 tgtgccacca cctggccggg ctgcagcaga tcctcagcca cctgaccagg gacaccgccg    360
ccctgacgcg ccgctacagc cagatcctgg agcggatcag ccccggcgac gcgcagccca    420
gctggtgacc ccgcgcggct ccgctcagcg ccgcgggacg gggcggcctc cgagcggcgc    480
cggcagagcc gcggagccgt ctgcggggcc gtcccgcggt gccccgcggc tccgccgtgc    540
gctccgtcct cggagagcgc cgcgctgccg cgctgggctc ggacggagcc gtgcggcgcc    600
ggcgccttcg ggctggatcc cggagccgcg cagcgctgcc ctctctcgtg ttttctaata    660
aaactcgtgt ttttccgcaa aaaa                                           684

<210> SEQ ID NO 4
<211> LENGTH: 135
<212> TYPE: PRT
<213> ORGANISM: Gallus gallus

<400> SEQUENCE: 4

Met Glu Arg Tyr Phe Ser Ala Thr Gln Lys Met Glu Gln Glu Val Met
1               5                   10                  15

Phe Pro Ser Leu Leu Arg Gly Val Phe Pro Gln Asp Gly Ala Asp Pro
            20                  25                  30

Ala Ala Asp Gly Pro Ala Asp Leu Tyr Glu Arg Tyr Gln Leu Leu Lys
        35                  40                  45

Ala Ile Lys Pro Val Val Glu Arg Gly Leu Ala Ser Phe Thr Glu Arg
    50                  55                  60

Ser Ser Ala Gly His Ala Asp Ala Asp Ala Glu Asp Ala Ala
65                  70                  75                  80

Ala Ala Ala Asp Gly Ala Ala Gly Ser Leu Glu Gln Arg Leu Cys His
                85                  90                  95

His Leu Ala Gly Leu Gln Gln Ile Leu Ser His Leu Thr Arg Asp Thr
            100                 105                 110

Ala Ala Leu Thr Arg Arg Tyr Ser Gln Ile Leu Glu Arg Ile Ser Pro
        115                 120                 125

Gly Asp Ala Gln Pro Ser Trp
    130                 135

<210> SEQ ID NO 5
<211> LENGTH: 146
<212> TYPE: PRT
<213> ORGANISM: Homo sapiens

<400> SEQUENCE: 5

Met Gln Val Leu Thr Lys Arg Tyr Pro Lys Asn Cys Leu Leu Thr Val
1               5                   10                  15

Met Asp Arg Tyr Ala Ala Glu Val His Asn Met Glu Gln Val Val Met
            20                  25                  30

Ile Pro Ser Leu Leu Arg Asp Val Gln Leu Ser Gly Pro Gly Gly Gln
        35                  40                  45

Ala Gln Ala Glu Ala Pro Asp Leu Tyr Thr Tyr Phe Thr Met Leu Lys
    50                  55                  60

Ala Ile Cys Val Asp Val Asp His Gly Leu Leu Pro Arg Glu Glu Trp
65                  70                  75                  80
```

Gln Ala Lys Val Ala Gly Ser Glu Glu Asn Gly Thr Ala Glu Thr Glu
                85                  90                  95

Glu Val Glu Asp Glu Ser Ala Ser Gly Glu Leu Asp Leu Glu Ala Gln
            100                 105                 110

Phe His Leu His Phe Ser Leu His His Ile Leu Met His Leu Thr
        115                 120                 125

Glu Lys Ala Gln Glu Val Thr Arg Lys Tyr Gln Glu Met Thr Gly Gln
    130                 135                 140

Val Trp
145

<210> SEQ ID NO 6
<211> LENGTH: 150
<212> TYPE: PRT
<213> ORGANISM: Mus musculus

<400> SEQUENCE: 6

Met Gln Val Leu Thr Lys Arg Tyr Pro Lys Asn Cys Leu Leu Thr Val
1               5                   10                  15

Met Asp Arg Tyr Ser Ala Val Val Arg Asn Met Glu Gln Val Val Met
            20                  25                  30

Ile Pro Ser Leu Leu Arg Asp Val Gln Leu Ser Gly Pro Gly Gly Ser
        35                  40                  45

Val Gln Asp Gly Ala Pro Asp Leu Tyr Thr Tyr Phe Thr Met Leu Lys
    50                  55                  60

Ser Ile Cys Val Glu Val Asp His Gly Leu Leu Pro Arg Glu Glu Trp
65                  70                  75                  80

Gln Ala Lys Val Ala Gly Asn Glu Thr Ser Glu Ala Glu Asn Asp Ala
                85                  90                  95

Ala Glu Thr Glu Glu Ala Glu Glu Asp Arg Ile Ser Glu Glu Leu Asp
            100                 105                 110

Leu Glu Ala Gln Phe His Leu His Phe Cys Ser Leu His His Ile Leu
        115                 120                 125

Thr His Leu Thr Arg Lys Ala Gln Glu Val Thr Arg Lys Tyr Gln Glu
    130                 135                 140

Met Thr Gly Gln Val Leu
145                 150

<210> SEQ ID NO 7
<211> LENGTH: 150
<212> TYPE: PRT
<213> ORGANISM: Rattus norvegicus

<400> SEQUENCE: 7

Met Gln Val Leu Thr Lys Arg Tyr Pro Lys Asn Cys Leu Leu Lys Val
1               5                   10                  15

Met Asp Arg Tyr Ser Ala Val Val Arg Asn Met Glu Gln Val Val Met
            20                  25                  30

Ile Pro Ser Leu Leu Arg Asp Val Glu Leu Met Gly Tyr Gly Gly Ser
        35                  40                  45

Val Gln Asp Gly Ala Pro Asp Leu Tyr Thr Tyr Phe Thr Met Leu Lys
    50                  55                  60

Ser Ile Cys Val Glu Val Asp His Gly Leu Leu Pro Arg Glu Glu Trp
65                  70                  75                  80

Gln Ala Lys Val Ala Gly Asn Glu Gly Ser Glu Ala Glu Asn Glu Ala
                85                  90                  95

```
Ala Glu Thr Glu Glu Ala Glu Asp Arg Leu Ser Glu Glu Leu Asp
            100                 105                 110

Leu Glu Ala Gln Phe His Leu His Phe Ser Ser Leu His His Ile Leu
        115                 120                 125

Thr His Leu Thr Gln Lys Ala Gln Glu Val Thr Gln Lys Tyr Gln Glu
    130                 135                 140

Met Thr Gly Gln Val Leu
145                 150

<210> SEQ ID NO 8
<211> LENGTH: 147
<212> TYPE: PRT
<213> ORGANISM: Danio rerio

<400> SEQUENCE: 8

Met Met Gln Ile Cys Asp Ser Tyr Asn Gln Lys Asn Ser Leu Phe Asn
1               5                   10                  15

Ala Met Asn Arg Phe Ile Gly Ala Val Asn Asn Met Asp Gln Thr Val
            20                  25                  30

Met Val Pro Ser Leu Leu Arg Asp Val Pro Leu Asp Gln Glu Glu Glu
        35                  40                  45

Lys Glu Val Thr Ser Phe Gln Asp Gly Asp Met Tyr Gly Ser Tyr Val
    50                  55                  60

Leu Leu Lys Ser Ile Arg Asn Asp Ile Glu Trp Gly Val Leu Gln Ala
65              70                  75                  80

Glu Glu Arg Arg Lys Glu Lys His Gly Val Thr Thr Thr Ser Leu Glu
                85                  90                  95

Val Ser Arg Ile Glu Pro Asn Asp Lys Asp Leu Glu Lys Leu Phe His
            100                 105                 110

Tyr His Leu Ser Gly Leu His Thr Val Leu Ala Lys Leu Thr Arg Lys
        115                 120                 125

Ala Asn Thr Leu Thr Asn Arg Tyr Lys Gln Glu Ile Gly Ile Gly Gly
    130                 135                 140

Cys Gly Asn
145

<210> SEQ ID NO 9
<211> LENGTH: 152
<212> TYPE: PRT
<213> ORGANISM: Danio rerio

<400> SEQUENCE: 9

Met Gln Met Ser Glu Pro Leu Ser Gln Lys Asn Ala Leu Tyr Thr Ala
1               5                   10                  15

Met Asn Arg Phe Leu Gly Ala Val Asn Asn Met Asp Gln Thr Val Met
            20                  25                  30

Val Pro Ser Leu Leu Arg Asp Val Pro Leu Asp Gln Glu Lys Glu Gln
        35                  40                  45

Gln Lys Leu Thr Asn Asp Pro Gly Ser Tyr Leu Arg Glu Ala Glu Ala
    50                  55                  60

Asp Met Tyr Ser Tyr Tyr Ser Gln Leu Lys Ser Ile Arg Asn Asn Ile
65              70                  75                  80

Glu Trp Gly Val Ile Arg Ser Glu Asp Gln Arg Lys Lys Asp Thr
                85                  90                  95

Ser Ala Ser Glu Pro Val Arg Thr Glu Glu Glu Ser Asp Met Asp Leu
            100                 105                 110
```

Glu Gln Leu Leu Gln Phe His Leu Lys Gly Leu His Gly Val Leu Ser
        115                 120                 125

Gln Leu Thr Ser Gln Ala Asn Asn Leu Thr Asn Arg Tyr Lys Gln Glu
130                 135                 140

Ile Gly Ile Ser Gly Trp Gly Gln
145                 150

<210> SEQ ID NO 10
<211> LENGTH: 165
<212> TYPE: PRT
<213> ORGANISM: Danio rerio

<400> SEQUENCE: 10

Met Met Gln Leu Ser Asn Asp Ser His Cys Asn Lys His Ser Leu Leu
1               5                   10                  15

Asn Val Met Asn Arg Phe Ile Ala Ala Asn Asn Met Asp Glu Thr
            20                  25                  30

Ile Met Val Pro Asn Leu Leu Arg Asp Val Pro Leu Asp Gln Glu
            35                  40                  45

Ser His Ala Ser Val Ser His Asn Asn Asn Asn Asn Glu Pro Ser
        50                  55                  60

Phe Pro Asn Lys Gln Arg Asp Met Tyr Glu His Tyr Leu Leu Lys
65                  70                  75                  80

Ser Ile Lys Asn Asp Met Glu Trp Gly Leu Leu Lys Arg Glu Met Ala
                85                  90                  95

Gly Gly Ala Ser Phe Leu Glu Met Ala Val Lys Gln Glu Glu Leu Pro
            100                 105                 110

Gln Met Lys Gly Glu Ala Val Glu Glu Gly Pro Asp Leu Glu Gly Gln
            115                 120                 125

Phe His Tyr His Leu His Gly Leu Phe Ser Val Leu Ser Lys Leu Thr
        130                 135                 140

Val Gln Ala Asp His Leu Thr Asn Arg Tyr Lys Arg Glu Ile Gly Gly
145                 150                 155                 160

Gly Ser Leu Leu Arg
            165

<210> SEQ ID NO 11
<211> LENGTH: 183
<212> TYPE: PRT
<213> ORGANISM: Homo sapiens

<400> SEQUENCE: 11

Met Met Gln Ile Cys Asp Thr Tyr Asn Gln Lys His Ser Leu Phe Asn
1               5                   10                  15

Ala Met Asn Arg Phe Ile Gly Ala Val Asn Asn Met Asp Gln Thr Val
            20                  25                  30

Met Val Pro Ser Leu Leu Arg Asp Val Pro Leu Ala Pro Gly Leu
        35                  40                  45

Asp Asn Asp Val Gly Val Glu Val Gly Gly Ser Gly Gly Cys Leu Glu
        50                  55                  60

Glu Arg Thr Pro Pro Val Pro Asp Ser Gly Ser Ala Asn Gly Ser Phe
65                  70                  75                  80

Phe Ala Pro Ser Arg Asp Met Tyr Ser His Tyr Val Leu Leu Lys Ser
                85                  90                  95

Ile Arg Asn Asp Ile Glu Trp Gly Val Leu His Gln Pro Pro Pro
            100                 105                 110

-continued

Ala Gly Ser Glu Glu Gly Ser Ala Trp Lys Ser Lys Asp Ile Leu Val
        115                 120                 125

Asp Leu Gly His Leu Glu Gly Ala Asp Ala Gly Glu Glu Asp Leu Glu
    130                 135                 140

Gln Gln Phe His Tyr His Leu Arg Gly Leu His Thr Val Leu Ser Lys
145                 150                 155                 160

Leu Thr Arg Lys Ala Asn Ile Leu Thr Asn Arg Tyr Lys Gln Glu Ile
                165                 170                 175

Gly Phe Gly Asn Trp Gly His
            180

<210> SEQ ID NO 12
<211> LENGTH: 182
<212> TYPE: PRT
<213> ORGANISM: Mus musculus

<400> SEQUENCE: 12

Met Met Gln Ile Cys Asp Thr Tyr Asn Gln Lys His Ser Leu Phe Asn
1               5                   10                  15

Ala Met Asn Arg Phe Ile Gly Ala Val Asn Asn Met Asp Gln Thr Val
            20                  25                  30

Met Val Pro Ser Leu Leu Arg Asp Val Pro Leu Ser Glu Pro Glu Ile
        35                  40                  45

Asp Glu Val Ser Val Glu Val Gly Gly Ser Gly Gly Cys Leu Glu Glu
    50                  55                  60

Arg Thr Thr Pro Ala Pro Ser Pro Gly Ser Ala Asn Glu Ser Phe Phe
65                  70                  75                  80

Ala Pro Ser Arg Asp Met Tyr Ser His Tyr Val Leu Leu Lys Ser Ile
                85                  90                  95

Arg Asn Asp Ile Glu Trp Gly Val Leu His Gln Pro Ser Ser Pro Pro
            100                 105                 110

Ala Gly Ser Glu Glu Ser Thr Trp Lys Pro Lys Asp Ile Leu Val Gly
        115                 120                 125

Leu Ser His Leu Glu Ser Ala Asp Ala Gly Glu Glu Asp Leu Glu Gln
    130                 135                 140

Gln Phe His Tyr His Leu Arg Gly Leu His Thr Val Leu Ser Lys Leu
145                 150                 155                 160

Thr Arg Lys Ala Asn Ile Leu Thr Asn Arg Tyr Lys Gln Glu Ile Gly
                165                 170                 175

Phe Ser Asn Trp Gly His
            180

<210> SEQ ID NO 13
<211> LENGTH: 159
<212> TYPE: PRT
<213> ORGANISM: Homo sapiens

<400> SEQUENCE: 13

Met Gln Ile Cys Asp Ser Tyr Ser Gln Lys Tyr Ser Leu Phe Asn Ala
1               5                   10                  15

Met Asn Arg Phe Ile Gly Ala Val Asn Asn Met Asp Gln Thr Val Met
            20                  25                  30

Val Pro Ser Leu Leu Arg Asp Val Pro Leu Leu Leu Gly Glu Leu Asp
        35                  40                  45

Ala Ala Gly Ala Val Cys Pro Glu Arg Glu Ala Pro Gly Gly Ala
    50                  55                  60

```
Tyr Phe Ser Arg Arg Asp Met Tyr Ser His Tyr Val Leu Leu Lys Ser
 65                  70                  75                  80

Ile Arg Asn Asp Ile Glu Trp Gly Val Val Gln Gln Ala Ala Gly Glu
                 85                  90                  95

Glu Ala Ala Arg Lys Asp Lys Leu Gly Gly Gly Pro Ala Glu Glu
            100                 105                 110

Ala Glu Ala Glu Glu Asp Leu Glu Gln Gln Phe His Tyr His Leu Ser
        115                 120                 125

Gly Leu His Thr Val Leu Ser Lys Leu Thr Arg Lys Ala Asn Val Leu
    130                 135                 140

Thr Asn Arg Tyr Lys Gln Glu Ile Gly Phe Gly Ser Trp Gly Gln
145                 150                 155
```

<210> SEQ ID NO 14
<211> LENGTH: 24
<212> TYPE: DNA
<213> ORGANISM: Gallus gallus

<400> SEQUENCE: 14
gtgcatttat cagaccaaaa ccaa                                         24

<210> SEQ ID NO 15
<211> LENGTH: 18
<212> TYPE: DNA
<213> ORGANISM: Gallus gallus

<400> SEQUENCE: 15
gcgatcggct cgaggtta                                                18

<210> SEQ ID NO 16
<211> LENGTH: 18
<212> TYPE: DNA
<213> ORGANISM: Gallus gallus

<400> SEQUENCE: 16
gcctccgtca ccgatcag                                                18

<210> SEQ ID NO 17
<211> LENGTH: 19
<212> TYPE: DNA
<213> ORGANISM: Gallus gallus

<400> SEQUENCE: 17
cggtcagaac ctgctgcaa                                               19

<210> SEQ ID NO 18
<211> LENGTH: 17
<212> TYPE: DNA
<213> ORGANISM: Gallus gallus

<400> SEQUENCE: 18
gcgtccttca ccgagcg                                                 17

<210> SEQ ID NO 19
<211> LENGTH: 20
<212> TYPE: DNA
<213> ORGANISM: Gallus gallus

<400> SEQUENCE: 19
tggctgagga tctgctgcag                                              20

```
<210> SEQ ID NO 20
<211> LENGTH: 20
<212> TYPE: DNA
<213> ORGANISM: Gallus gallus

<400> SEQUENCE: 20
cgtgtggatg gcaagatgtt                                              20

<210> SEQ ID NO 21
<211> LENGTH: 20
<212> TYPE: DNA
<213> ORGANISM: Gallus gallus

<400> SEQUENCE: 21
caactccagg cttgctgcat                                              20

<210> SEQ ID NO 22
<211> LENGTH: 20
<212> TYPE: DNA
<213> ORGANISM: Gallus gallus

<400> SEQUENCE: 22
gccttgttgt ttgtgcgttg                                              20

<210> SEQ ID NO 23
<211> LENGTH: 21
<212> TYPE: DNA
<213> ORGANISM: Gallus gallus

<400> SEQUENCE: 23
aaatgccctg tggttgtcag a                                            21

<210> SEQ ID NO 24
<211> LENGTH: 18
<212> TYPE: DNA
<213> ORGANISM: Gallus gallus

<400> SEQUENCE: 24
ttctcggcca cgcagaag                                                18

<210> SEQ ID NO 25
<211> LENGTH: 18
<212> TYPE: DNA
<213> ORGANISM: Gallus gallus

<400> SEQUENCE: 25
aagacccctc gcagcagg                                                18
```

IDENTIFICATION OF FAT AND LEAN PHENOTYPES IN CHICKENS USING MOLECULAR MARKERS

This application claims the benefit of provisional application Ser. No. 60/530,051 filed Dec. 16, 2003, which is hereby incorporated by reference.

REFERENCE TO U.S. GOVERNMENT SUPPORT

This work is supported by a grant from the USDA-IFAFS, Animal Genome Program (Award Number 00-52100-9614). The United States government has certain rights in the invention.

FIELD OF THE INVENTION

The present invention relates to methods for identifying the phenotype of a chicken using a genetic polymorphism associated with a fat or lean phenotype. More particularly the invention relates to methods of identifying a fat or lean chicken phenotype by determining the presence of an insertion/deletion associated with a fat or lean phenotype in one or both of the duplicated chicken Spot 14 genes, also referred to as thyroid hormone responsive Spot 14 protein (THRSPα and THRSPβ) paralogs.

BACKGROUND OF THE INVENTION

Over the last decades intensive selection on growth rate has been done in broiler chicken strains developed for meat production. However, fatness has also been increased, leading to excessive adiposity. By reducing feed efficiency and lean meat yield, this excess of fat tissue is a major drawback for production.

In order to decipher the metabolic and genetic mechanisms involved in the regulation of fatness in the chicken, some investigators have developed experimental models of adiposity. Lean and fat chicken lines have been divergently selected from adipose tissue weight (Leclerq et al., 1980) and for very low density lipoprotein (VLDL) plasma concentration (Whitehead, C. C., Griffin, H. D., 1984). Studies performed in lean and fat lines developed by Leclercq et al (1980) indicate that the difference in adiposity between lines was not the result of a difference in food consumption or in nutrient utilization. Stearoyl-Co-A desaturase activity and plasma VLDL concentration were found to be higher in the fat line (Legrand, P. and Hermier, D., 1992), suggesting a higher lipogenesis rate in this line.

In the chicken, lipogenesis occurs essentially in the liver, the adipose tissue being only a storage tissue (O'Hea, E. K. and Leveille, G. A., 1968; Griffin et al., 1992).

The Spot 14 gene, also referred to as thyroid hormone responsive Spot 14 protein (THRSP), encodes a small acidic protein that was discovered in earlier studies of thyroid hormone action on hepatocytes (Seelig et al., 1981; Jump et al., 1984; Liaw and Towle, 1984). Although the exact molecular mechanism is not clear, THRSP is strongly implicated as a transcription factor that controls expression of major lipogenic enzymes. For instance, THRSP is only expressed in lipogenic tissue such as liver, fat and the mammary gland (Liaw and Towle, 1984; Jump and Oppenheimer, 1985). THRSP mRNA levels are greatly increased by carbohydrate feeding or insulin-injection and decreased by high plasma glucagon levels or by feeding a diet rich in polyunsaturated fatty acids (Jump et al., 1993). Hepatocytes transfected with a THRSP antisense oligonucleotide express decreased mRNA levels in enzymes involved in the lipogenic pathway [i.e., ATP-citrate lyase (ACLY), fatty acid synthase (FAS) and malic enzyme (ME)] (Kinlaw et al., 1995; Brown et al., 1997). Although an increase in lipogenesis was observed in the THRSP knockout mouse, this contradiction could be due to incomplete gene deletion or overcompensation by alternative pathways (Zhu et al., 2001). Homodimers of THRSP interact with and activate chicken ovalbumin upstream promoter-transcription factor 1 (COUP-TF1) in promoting transcription of L-type pyruvate kinase (L-PK) through an interaction with specificity protein 1 (Spl) (Compe et al., 2001). Furthermore, the THRSP promoter region contains three thyroid response elements (TREs) that work synergistically and interact with far upstream region (FUR) elements to maximize triuodothyronine ($T_3$) responses in hepatocytes (Liu and Towle, 1994). Apparently, the human THRSP promoter responds more robustly to $T_3$ than glucose, while the rat THRSP promoter region is more responsive to glucose than $T_3$ (Campbell et al, 2003).

Many common diseases and conditions are not caused by a genetic variation within a single gene, but are influenced by complex interactions among multiple genes as well as environmental and lifestyle factors. Genetic predisposition is the potential of an individual to develop a disease or condition based on genes and hereditary factors. Although both environmental and lifestyle factors add tremendously to the uncertainty of developing a disease, it is currently difficult to measure and evaluate their overall effect on a disease process. By studying changes within a gene that have been found to be associated with a disease trait, researchers may begin to reveal relevant genes associated with a disease. Polymorphisms can thus serve as biological markers for a disease or trait associated with a disease. Therefore, it is desirable to find polymorphism(s) which can be used for the diagnosis of a disease (including metabolic diseases such as obesity) and/or identification of a trait, such as polymorphisms associated with a fat or lean chicken phenotype.

SUMMARY OF THE INVENTION

The invention provides methods of screening chickens to determine those more likely to have a lean or fat phenotype comprising the steps of obtaining a sample of genetic material from a chicken; and identifying in the genetic material the presence of at least one insertion or deletion of nucleotides associated with a fat phenotype or a lean phenotype in the sequence encoding one or both of the chicken thyroid hormone responsive Spot 14 protein (THRSP) paralogs, THRSPα (SEQ ID NO: 1) and THRSPβ (SEQ ID NO: 3).

The invention also provides methods of screening chickens to identify a polymorphism associated with a fat or lean phenotype comprising obtaining a sample of genetic material from a chicken; and identifying in the genetic material the presence of at least one insertion or deletion of nucleotides in the sequence encoding one or both of the chicken thyroid hormone responsive Spot 14 protein (THRSP) paralogs, THRSPα (SEQ ID NO: 1) and THRSPβ (SEQ ID NO: 3), that is associated with a fat phenotype or a lean phenotype.

Preferably, the insertion or deletion is the insertion or deletion of the sequence ATAGATGGC in THRSPα (bases 261-269 of the sequence shown in FIG. 1A) and/or the insertion or deletion of the sequence GCCGAC in THRSPβ (bases 228-233 of the sequence shown in FIG. 1B). The polymorphisms found in THRSPα and THRSPβ involve a region of nucleotide sequence known as variable number of tandem repeats (VNTRs) For example, the sequence ATAGATGGC is repeated twice in THRSPα, (bases 261-279 of the sequence shown in FIG. 1A) and the sequence GCCGAC is repeated three times in THRSPβ (bases 228-245 of the sequence shown in FIG. 1B).

The insertion/deletion of bases in THRSPα (FIG. 1A) (SEQ ID NO: 1) and THRSPβ (FIG. 1B) (SEQ ID NO: 3) is enclosed in a box. In the insertion alleles of THRSPα and THRSPβ, the boxed bases are present. In the deletion alleles of THRSPα and THRSPβ, the boxed bases are absent.

Preferably, the step of identifying the presence of the polymorphism comprises the steps of: amplifying at least one portion of the nucleotide sequence encoding THRSPα (SEQ ID NO: 1) or THRSPβ (SEQ ID NO: 3) or both, in which the region contains an insertion or deletion that is associated with a fat phenotype or lean phenotype, and detecting the insertion or deletion in the at least one amplified portion.

These and other aspects of the invention are set out in the following Detailed Description and in the appended claims.

BRIEF DESCRIPTION OF THE DRAWINGS

FIG. 1 shows the cDNA sequence and predicted protein sequence of the chicken THRSP paralogs. (A) THRSPα cDNA (SEQ ID NO: 1) and its predicted protein sequence (SEQ ID NO: 2). Primer sequences used for PCR are indicated by the bold underlined letters. The predicted leucine zipper motif is shown in bold letters and the poly(A) signal is underlined. The boxes represent the missing nt and aa residues in the deletion allele ($\alpha_2$). Sequence encoded by the 5'-UTR and 3'-UTR (exon 2) is shown in lower case letters. The asterisk shows the stop codon. The junction between exons 1 and 2 is indicated by the inverted solid triangle. (B) THRSPβ cDNA (SEQ ID NO: 3) and its predicted protein sequence (SEQ ID NO: 4). Primer sequences used for PCR are indicated by the bold underlined letters. The predicted leucine zipper motif is shown in bold letters and the poly(A) signal is underlined. The boxes represent the missing nt and aa residues in the deletion allele ($\beta_2$). Sequence encoded by the 5'-UTR is shown in lower case letters and the 3'-UTR (exon 2) is shown in uppercase letters. The asterisk shows the stop codon.

FIG. 2 shows protein sequence alignment of the Spot 14 family members: the THRSPs, gastrulation specific [zebrafish]G12 proteins, and the hypothetical [human] STRAIT11499 proteins. Protein sequences for chicken [c] THRSP.alpha. (UD CAP3 Contig.sub.—8452.1) (SEQ ID NO: 2) and THRSP.beta. (UD CAP3 Contig.sub.—8452.2) (SEQ ID NO: 4), human [h] THRSP (AAH31989) ((SEQ ID NO: 5), mouse [m] THRSP (Q62264) (SEQ ID NO: 6), rat [r] THRSP (PO.sub.4143) (SEQ ID NO: 7) and zebrafish [z] (zTC192887) (SEQ ID NO: 10) THRSP were aligned using ClustalW with default parameters and BLOSUM62 scoring matrix. This alignment includes two structurally related proteins: gastrulation-specific protein G12 from zebrafish (zG12)(SEQ ID NO: 9) (P47805) and an apparently duplicated G12 protein (zTC194742) (SEQ ID NO:8) found in the database of the Institute for Genomic Research (TIGR) (TIGR.org) which show a high degree of structural similarity to the hypothetical [human] hSTRAIT11499 protein (AAH19332) (SEQ ID NO: 11), mSTRAIT11499 (Q9CQ20) (SEQ ID NO: 12), cSTRAIT11499 (derived from UD CAP3 Contig.sub.—22252.1) (SEQ ID NO: 13). Identical amino acid (aa) residues are shown black, similar (positive) amino acid (aa) residues are shown in gray and the hyphens denote gaps.

FIG. 4 shows the genomic organization of the chicken THRSP paralogs. (A) Southern blot analysis of the THRSP gene. Genomic DNA was digested to completion with restriction enzymes and hybridized with a probe (pgf2n.pk005.j11) common to both THRSPα and THRSPβ cDNAs. Two restriction fragments were expected after PstI digestion. The darker band represents THRSPα because it corresponds to the full-length probe, while only 230 bp of the probe corresponds to the THRSPβ cDNA (lighter band). (B) Putative restriction map of genomic DNA harboring the THRSP paralogs. The direction of transcription is indicated by the arrows. The exact distance between THRSPα and THRSPβ is unknown (dashed line). Open boxes represent location of the probe used in the Southern blot (A) above. [Abbreviations used: H, HindIII; B, BamHI; and P, PstI.] (C) The genomic structure of THRSPα, which includes a TATA box. Exon 1 represents the short 5'-UTR and the protein coding region, while exon 2 represents the 3'-UTR.

FIG. 6 shows expression of THRSP transcripts in chicken tissues. Total RNA (40 ng per reaction) was analyzed by real-time qRT-PCR (Applied Biosystems (ABI)) using TaqMan by a universal QuantiTech Sybr Green qRT-PCR kit (Qiagen). Primers were designed using Primer Express 2.0 software (Applied Biosystems (ABI)). (A) Expression of total THRSP in 11 tissues using common primers (32F/93R). Values represent the mean±SEM of duplicate determinations in arbitrary units (AU). RNA from most tissues was isolated from 5-week-old broiler chickens. RNA was extracted from the thymus and epiphyseal growth plate of 3-week-old broiler chickens. Testes and ovary RNA was isolated from 8-week-old Leghorn chickens; RNA was also collected from the ovary of an adult (1 year old) Leghorn hen. (B) Expression of THRSPα and THRSPβ in fat and liver of 5-week-old broiler chickens. (C) Expression of THRSP mRNAs in the liver during the peri-hatch period [Day 20 embryos (e20) and 1 day old (1 da) chicks]. Each value represents the mean±SEM of four embryos and four chicks. (D) The response of hepatic THRSPα and THRSPβ mRNAs to changes in nutritional state. Liver samples were collected from a fast-growing strain of French (INRA) broiler chickens at six weeks of age after a 48 h fast (S48) and at 4 h post re-feeding (RF4) following the 48 h fast (Beccavin et al, 2001). Each value represents the mean±SEM of four birds.

DETAILED DESCRIPTION OF THE INVENTION

Figure 3:
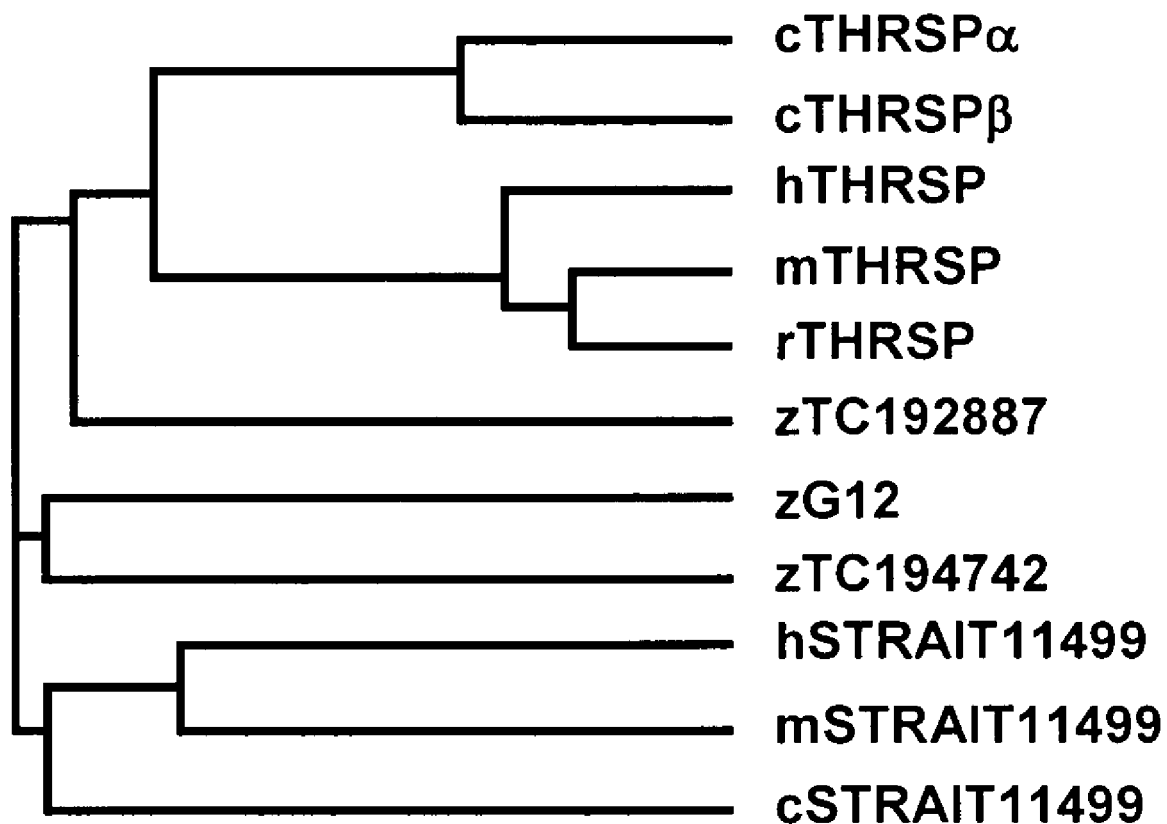
FIG. 3 shows a dendrogram of the phylogenetic relationship among Spot 14 family members: the THRSPs, the gastrulation-specific [zebrafish] G12 proteins, and hypothetical [human] STRAIT11499 proteins. The phylogenetic tree was created using the ClustalW program with default settings and the BLOSUM62 scoring matrix.

The methods of the invention are useful for identifying individual chickens or groups of chickens that have a predisposition for a lean or fat phenotype. Identification of birds having a lean or fat phenotype is of interest to chicken breeders and growers for use in marker assisted selection (MAS) breeding programs. Insertions/deletions in one or both of the genes encoding the THRSP paralogs (THRSPα and THRSPβ), also known as Spot 14, are useful as a genetic markers for MAS programs in poultry breeding. A chicken's phenotype (lean or fat) can be determined from tissue or blood samples even before the chick is hatched, without the need for raising potential breeder chickens to adult age for measurement of the phenotype.

Applicants have discovered that THRSP, sometimes referred to as Spot 14, has two forms, α and β paralogs, in chickens and that an insertion/deletion in one or more of the paralogs is correlated with a fat or lean phenotype. Chicken Spot 14 (THRSP) was first identified as a differentially-expressed EST (pat.pk0032.c9.f) from microarray analysis of livers from chickens divergently selected for fast or slow growth rate (Cogburn et al., 2000; Cogburn et al., 2003a). An EST was discovered by differential mRNA display in liver of genetically fat and lean chickens and subsequently mapped to chicken Chr1q41-44 (Carre et al., 2001). This EST was identified as chicken THRSP from alignment with an annotated EST (pat.pk0072.c10.f) in the University of Delaware (UD) chicken EST database. This chromosomal region in chickens also harbors quantitative trait loci (QTL) for skin fatness (Ikeobi et al., 2002) and abdominal fatness (Lagarrigue et al., 2003).

One aspect of the invention therefore provides a method of screening chickens to determine those more likely to have a lean or fat phenotype comprising the steps of: obtaining a sample of genetic material from a chicken; and identifying the presence of insertions or deletions of bases in the nucleotide sequence encoding the duplicated chicken thyroid hormone responsive Spot 14 protein (i.e., the THRSPα and THRSPβ paralogs), which sequences are set out in FIG. 1A (SEQ ID NO: 1) and 1B (SEQ ID NO: 3), that are associated with a fat phenotype or a lean phenotype. Preferably, the methods of the invention detect an insertion/deletion of a nine base sequence in the THRSPα nucleotide sequence shown in FIG. 1A (SEQ ID NO: 1), wherein the nine base VNTR sequence is ATAGATGGC (bases 261-269 of the sequence shown in FIG. 1A (SEQ ID NO: 1)) and/or an insertion/deletion of six to twelve bases in the THRSPβ nucleotide sequence shown in FIG. 1B (SEQ ID NO: 3), wherein the six base VNTR sequence is GCCGAC in THRSPβ (bases 228-233 of the sequence shown in FIG. 1B (SEQ ID NO: 3)).

Another aspect of the invention provides a method of screening chickens to identify a polymorphism associated with a fat or lean phenotype comprising the steps: of obtaining a sample of genetic material from a chicken; and identifying the presence of one or more insertions or deletions of nucleotides associated with a fat phenotype or a lean phenotype in the sequence encoding one or both of the THRSP paralogs. The nucleotide sequence encoding THRSPα is set out in SEQ ID NO: 1 in FIG. 1A and the nucleotide sequence encoding THRSPβ is set out in SEQ ID NO: 3 in FIG. 1B.

Preferably, the methods of the invention identify an insertion/deletion of a nine base sequence in the sequence encoding THRSP, wherein the nine base VNTR sequence is ATAGATGGC (bases 261-269 of the sequence shown in FIG. 1A (SEQ ID NO: 1)) and/or an insertion/deletion of six to twelve bases in the THRSPβ nucleotide sequence shown in FIG. 1B, wherein the six base VNTR sequence is GCCGAC in THRSPβ (bases 228-233 of the sequence shown in FIG. 1B (SEQ ID NO: 3)).

Fat phenotype refers to a phenotype wherein abdominal fat is about 3-4% (or greater) of body weight. Lean phenotype refers to a phenotype wherein abdominal fat is about 1 to 1.2% (or less) of body weight. Abdominal fat is measured by measuring the live body weight (in g or kg), killing the bird, careful dissection of the abdominal fat pad including that surrounding the ventriculus (gizzard) and that surrounding the cloaca (rectum), then measuring the weight of the dissected abdominal fat pad, and is expressed as percent of body weight (% BW). However, Whitehead, C. C., Griffin, H. D. (1984), have divergently selected lean and fat lines of chickens based on low or high plasma very low density lipoprotein (VLDL) levels, respectively. These fat and lean lines of chickens differ in their abdominal fat content (g/kg BW) by only 49%. Thus, the degree of leanness or fatness selected in a given population of chickens could vary depending on the genetic background and the selection criteria. Therefore, the definition of leanness or fatness should be based on a phenotypic difference in the average abdominal fat content (% BW) with a difference of least two standard error units.

Genetic material used in the methods of the invention may be isolated from cells, tissues, blood or other samples according to standard methodologies, such as the methods in Sambrook et al., *Molecular Cloning: A Laboratory Manual*, Cold Spring Harbor Laboratory Press, Cold Spring Harbor, N.Y., (1989). In certain embodiments, analysis is performed on whole cell or tissue homogenates or biological fluid samples without substantial purification of the template nucleic acid. The genetic material may be DNA or RNA. Where RNA is used, it may be desired to first convert the RNA to a complementary DNA. A preferred source of genetic material is blood. Chickens have nucleated red blood cells which makes blood a convenient source of genetic material (i.e., genomic DNA).

The polymorphism indicative of a fat or lean phenotype described herein can be identified by any method known in the art that can be used for detecting insertions or deletions within a nucleic acid sequence. A preferred method is a polymerase chain reaction (PCR)-based assay followed by separation of the amplification products by gel electrophoresis. Another preferred method is a PCR-based assay using TaqMan® or molecular beacon probes to detect the amplified target region.

A number of template dependent processes are available to amplify the oligonucleotide sequences present in a given template sample. One of the best-known amplification methods is the polymerase chain reaction (referred to as PCR) which is described in detail in U.S. Pat. Nos. 4,683,195, 4,683,202 and 4,800,159, each of which is incorporated herein by reference in their entirety.

A reverse transcriptase PCR (RT-PCR) amplification procedure may be performed to quantify the amount of mRNA amplified. Methods of reverse transcribing RNA into cDNA are well known and described in Sambrook et al., *Molecular Cloning: A Laboratory Manual*, Cold Spring Harbor Laboratory Press, Cold Spring Harbor, N.Y., (1989). Alternative methods for reverse transcription utilize thermostable DNA polymerases. These methods are described in WO 90/07641.

Polymerase chain reaction methodologies are well known in the art. Representative methods of RT-PCR are described in U.S. Pat. Nos. 5,882,864, 5,673,517 and 5,561,058.

After amplification, the insertion/deletion can be detected by methods known in the art such as separation of the amplification products by gel electrophoresis, sequencing of the amplification products, or hybridization with a nucleic acid probe.

Any sequencing method known to a person skilled in the art may be employed. In particular, it is advantageous to use an automated DNA sequencer. The sequencing is preferably carried out with a double-stranded template by means of the chain-termination method using fluorescent primers. An appropriate kit for this purpose is provided from PE Applied Biosystems (PE Applied Biosystems, Norwalk, Conn., USA).

Methods of gel electrophoresis are well known in the art. The number of bases in the separated amplification products can be determined by reference to markers of known nucleotide length.

The invention also provides primers and probes for use in the assays to detect the insertion/deletion. The primers and probes are based on and selected from the nucleotide sequence of THRSPα set out in FIG. 1A (SEQ ID NO: 1) and of THRSPβ set out in FIG. 1B (SEQ ID NO: 3), and will typically span the region of THRSPα or THRSPβ sequence upstream or downstream of the insertion/deletion sites, or span the insertion/deletion site in the case of a probe and will have a length appropriate for the particular detection method. One aspect of the invention thus provides oligonucleotides comprising from about 10 to about 30 contiguous bases of the nucleotide sequence encoding THRSPα (FIG. 1A) and/or of THRSPβ (FIG. 1B) or the complementary sequence for use as probes or primers. Primers that will be used in assays to quantitate Spot 14 mRNA can be selected from any portion of the THRSPα or THRSPβ nucleotide sequence shown in FIGS. 1A and 1B that will provide reliable amplification of Spot 14 paralog nucleic acid. Presently preferred primers include the primers set out in Table 1 (THRSP α, THRSP β and total THRSP primers). The length of the oligonucleotide primers are commonly in the range of 10 to 30 nucleotides in length, preferably in the range of 18 to 25 nucleotides in length.

Probes can be any length suitable for specific hybridization to the target nucleic acid sequence. The most appropriate length of the probe may vary depending upon the hybridization method in which it is being used; for example, particular lengths may be more appropriate for use in microfabricated arrays (microarrays), while other lengths may be more suitable for use in classical hybridization methods. Such optimizations are known to the skilled artisan. Suitable probes can range from about 5 nucleotides to about 30 nucleotides in length. Additionally, a probe can be a genomic fragment that can range in size from about 25 to about 2,500 nucleotides in length. The probe preferably overlaps at least one polymorphic site occupied by any of the possible variant nucleotides. The nucleotide sequence of the probe can correspond to the coding sequence of the allele or to the complement of the coding sequence of the allele.

Preferably, the PCR probes are TaqMan® probes which are labeled at the 5'end with a fluorophore, and at the 3'-end with a quencher or a minor groove binder and a quencher (for minor groove binding assays), or molecular beacon probes. TaqMan probes, suitable fluorophores and quenchers for use with TaqMan® probes and PCR methods employing TaqMan probes are disclosed in U.S. Pat. Nos. 5,210,015, 5,804,375, 5,487,792 and 6,214,979.

Hybridizations can be performed under stringent conditions, e.g., at a salt concentration of no more than 1 M and a temperature of at least 25.degree. C. For example, conditions of 5×SSPE (750 mM NaCl, 50 mM Na-Phosphate, 5 mM EDTA, pH 7.4) and a temperature of 25-30.degree. C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

The reaction mixture for amplifying the DNA comprises 4 deoxynucleotide phosphates (dATP, dGTP, dCTP, dTTP) and heat stable DNA polymerase (such as Taq polymerase), which are all known to the skilled person in the art.

The oligonucleotide primers and probes can be synthesized by any technique known to a person skilled in the art, based on the structure of the nucleotide sequence of THRSP or its complement.

The term "isolated" oligonucleotide refers to an oligonucleotide that is found in a condition other than its native environment. In a preferred form, the oligonucleotide is substantially free from other nucleic acid sequences, such as other chromosomal and extrachromosomal DNA and RNA, that normally accompany or interact with it as found in its naturally occurring environment. The term "isolated" oligonucleotide also embraces recombinant oligonucleotides and chemically synthesized oligonucleotides.

The invention further provides kits comprising at least one set of primers for amplifying a region of the nucleotide sequence of THRSPα and/or THRSPβ that span the insertion/deletion sites. The assay kit can further comprise the four deoxynucleotide phosphates (dATP, dGTP, dCTP, dTTP) and an effective amount of a nucleic acid polymerizing enzyme. A number of enzymes are known in the art which are useful as polymerizing agents. These include, but are not limited to *E. coli* DNA polymerase I, Klenow fragment, bacteriophage T7 RNA polymerase, reverse transcriptase, and polymerases derived from thermophilic bacteria, such as *Thermus aquaticus*. The latter polymerases are known for their high temperature stability, and include, for example, the Taq DNA polymerase I. Other enzymes such as Ribonuclease H can be included in the assay kit for regenerating the template DNA. Other optional additional components of the kit include, for example, means used to label a probe and/or primer (such as a fluorophore, quencher, chromogen, etc.), and the appropriate buffers for reverse transcription, PCR, or hybridization reactions. Usually, the kit also contains instructions for carrying out the methods.

Synthetic chemistry techniques can be used to synthesize the oligonucleotides of the invention.

All patents and patent applications cited in the present application are expressly incorporated herein by reference for all purposes. The above disclosure generally describes the present invention. A more complete understanding can be obtained by reference to the following specific examples, which are provided for purposes of illustration only and are not intended to limit the scope of the invention.

EXAMPLES

Abbreviations: THRSP, thyroid hormone-responsive Spot 14 protein; aa, amino acid; bp, base pair; NDUFC2, NADH dehydrogenase; ALG8, glucosyltransferase; ACLY, ATP-citrate lyase; FAS, fatty acid synthase; ME, malic enzyme; COUP-TF1, chicken ovalbumin upstream promoter-transcription factor 1; L-PK, L-type pyruvate kinase; Sp 1, specificity protein 1; TRE, thyroid response elements; FUR, far upstream region; $T_3$, triuodothyronine; QTL, quantitative trait loci; CAP3, contig assembly program 3; UD, University of Delaware; CR1, chicken repeat 1; EST, expressed sequence tag; SSC, sodium chloride, sodium citrate; BAC, bacterial artificial chromosome; qRT-PCR, quantitative reverse transcriptase polymerase chain reaction; IGCRP, Iowa Growth and Composition Resources Population; BBSRC, British Biotechnology and Biological Sciences Research Council; UTR, untranslated region; indel, insertion/deletion; kDa, kilo Dalton; pI, isoelectric point; G12, gastrulation-specific protein; STRAIT11499, hypothetical human protein; SRE, sterol response element; SREBP1c, sterol response element binding protein 1c; ChoRE, carbohydrate response element.

1. Materials and Methods 1.1 Chicken EST Assembly and DNA Sequence Analyses

The in silico cDNA sequence of THRSP was assembled from chicken EST sequences generated from two international chicken EST projects (Boardman et al., 2002) (Cogburn et al., 2003b). and those found in public databases (GenBank). Contigs were assembled using CAP3 (Huang and Madan, 1999) with 40 bp overlap and 90% identity; the CAP3 assemblies and a chicken gene index are available from the University of Delaware, Chicken Gene Index (Larry A. Cogburn). Contig and unassembled singlet sequences were used in BlastN and BlastX searches for identification of chicken genes.

The in silico cDNA sequence of chicken THRSP was also used in BlastN searches against the GenBank chicken genome trace archive deposited by the Washington University Genome Center. The sequences of the Blast hits and their mate pairs were retrieved and used to build genomic contigs, which were then used in subsequent BlastN searches. This in silico chromosome walking procedure was repeated five times. The final genomic contigs and singlets were used to blast against our CAP3 database to identify genes in the vicinity of THRSPα and THRSPβ. To avoid multi-locus chicken repeat 1 (CR1) repetitive sequences, genomic regions containing CR1 sequences were carefully inspected.

For Southern blot analysis, chicken genomic DNA was extracted from liver and digested with restriction enzymes in buffer supplied by the manufacturer (Promega, Madison, Wis.). The digested DNA (25 μg) was then precipitated with ethanol and resuspended in water. Restriction fragments were then separated in 1% agarose gel and transferred onto a nylon membrane. A chicken THRSP probe was labeled with $^{32}$P-dCTP by PCR amplification of insert in a UD Spot 14 EST clone (pgf2n.pk005.j11) using 32F and DeletionR primers (see Table 1). Hybridization was carried out at 42° C. overnight in Dig Easy Hyb buffer (Roche; Indianapolis, Ind.) with the $^{32}$P-labeled probe (1×10$^6$ dpm/ml). After hybridization, the filter was sequentially washed in 1×SSC, 0.2×SSC and 0.1×SSC supplemented with 0.1% SDS at 62° C. for 15 min each. The membrane was exposed to a phosphor screen overnight and scanned with a phosphorImager (Storm 840, Molecular Dynamics).

1.2 Analysis of Two Chicken BAC Clones

Two chicken BAC clones (65J23 and 94A1) which were positive for chicken THRSP (Carre et al, 2001) were obtained from the Texas A&M University BAC Center. The BAC DNA was prepared using the Large Construct Kit (Qiagen, Valencia, Calif.). The primers for chicken NADH dehydrogenase (NDUFC2) and glucosyltransferase (ALG8) were designed from in silico cDNA sequences (UD CAP3 Contig_7797.2 and Contig_3078.1, respectively) which correspond to these chicken genes (see Table 1).

1.3 RNA Isolation and Real-Time Quantitative RT-PCR

Tissues of interest were taken immediately after cervical dislocation, snap frozen in liquid nitrogen and stored at −80° C. until extraction of RNA. Total RNA was extracted using a RNeasy midi kit (Qiagen; Valencia, Calif.) and its concentration determined by reading the optical density at 260 nm. Samples were diluted in RNase free water to a concentration of 20 ng/μl and stored in a 96-well plate at −80° C. Real-time quantitative RT-PCR (qRT-PCR) was performed with a 7900HT Sequence Detection System (TaqMan) (Applied Biosystems (ABI), Foster City, Calif.) using the TaqMan Master Mix Kit and gene-specific molecular beacon probes (Applied Biosystems (ABI)) for 18S and total THRSP (Table 1). Primers were designed using Primer Express 2.0 software (Applied Biosystems (ABI)). For the remaining four genes, the QuantiTech SYBR green RT-PCR kit (Qiagen, Valencia, Calif.) and gene-specific PCR primers (see Table 1) were used in 20 μl per reaction following protocols recommended by the manufacturer. The concentration of total RNA in each sample was ensured by analyzing 18S RNA by qRT-PCR, which showed no significant difference between samples. A standard curve and conversion factor between primer sets 32F/93R (detects both THRSPα and β) and DeletionF/DeletionR (α specific) were generated using a plasmid from a THRSP EST clone (pgf2n.pk005.j11) as template, which was diluted to the optimal concentration range (4.26×10$^4$ to 1.75×10$^8$ copies per μl) in water containing 20 ng/μl yeast RNA. The template was then amplified following a standard TaqMan qRT-PCR protocol (Applied Biosystems (ABI)). The expression of THRSPβ in chicken tissue was calculated by taking the difference between total THRSP (32F/93R primers) and THRSPα-specific (DeletionF/DeletionR primers) measurements.

1.4 Genotyping and Trait Association Analysis

The Iowa Growth and Composition Resources Population (IGCRP) were used to study the association of the THRSPα and THRSPβ polymorphisms with abdominal fat traits. This population was established by crossing a broiler sire (from a commercial broiler breeder male line) with dams from two unrelated highly-inbred lines (Leghorn G-B2 and Fayoumi M15.2). These two inbred lines are more than 99% inbred (Zhou and Lamont, 1999). Two $F_1$ male offspring of the same sire, one from each genetic cross ($F_1$ Leghorn and $F_1$ Fayoumi) were randomly selected and each rooster mated with 20 half-sib $F_1$ females, producing about 720 $F_2$ offspring in three hatches. Abdominal fat weight (Fat) was measured and also expressed as a percentage of body weight at 8 weeks of age (% Fat). For genotyping of THRSPα, genomic DNA samples (40 ng) were amplified by PCR using fluorescence forward primer 6FAM-DeletionF and reverse primer DeletionR at 0.2 μM each with 0.2 U Taq DNA polymerase and 1.5 mM MgCl$_2$ in 20 μl. PCR was performed for 35 cycles of 45 sec at 94° C., 45 sec at 55° C., and 60 sec at 72° C. after denaturation at 95° C. for 2 min. Final extension was carried out for 5 min. The 6FAM-DeletionF and reverse primer DeletionR produce a 127 or 136 bp amplicon as described in Table 1. The 136 bp amplicon is representative of THRSP α1 which is the THRSP α insertion. The 127 bp amplicon is representative of the THRSP α2 which is the THRSP α deletion.

PCR genotyping of the THRSPβ polymorphism was performed using ThermalAce PCR kit (Invitrogen; Carlsbad, Calif.), which is specifically designed to amplify very GC rich regions of DNA, and the ParalogF/ParalogR primers (Table 1). Thermal cycles were essentially the same as used in typing THRSPα, except that denaturation was at 98° C. The ParalogF/ParalogR primers produce a 145 or 151 bp amplicon as shown in Table 1. The 151 bp amplicon is representative of the THRSPβ1 which is the THRSP 62 insertion. The 145 bp amplicon is representative of THRSPβ2 which is the THRSP β deletion.

The JMP® program (SAS Institute; Cary, N.C.) (Sall and Lehman, 1996) was used to conduct the general linear model test for association between genotype and fat traits based on model for the whole $F_2$ population: $Y=\mu+G+Sex+Dam_{random}$ (Cross)+Hatch$_{random}$+e. Where Y is the dependent variable, μ is population mean, G is genotype, and e is the random error. For analysis of each genetic cross, the statistical model was the same except that Dam$_{random}$ was substituted for Dam$_{random}$(Cross), because the crosses were analyzed separately.

2. Results 2.1. Identification of THRSPα and THRSPβ Genes.

The in silico cDNA sequence (UD CAP3 Contig.sub.— 8452.1) of chicken THRSP.alpha. (FIG. 1) was assembled from a total of 61 ESTs found in the University of Delaware (UD) chicken EST database (chickest.udel.edu), the British Biotechnology and Biological Sciences Research Council (BBSRC) chick EST database (chick.Lmist.ac.ukl) (Boardman et al., 2002), and GenBank. The THRSPα contig sequence is 874 bp and it includes two closely located poly (A) signals in the 3'-UTR and a poly(A) tail. No additional sequence was found at the 5'-end of THRSPα by 5'-RACE analysis (Invitrogen). Northern blot analysis showed the THRSPα transcript is 1.1 kb (data not shown). The predicted size of the THRSPα peptide is either 129 or 132 aa (due to the 9-bp indel polymorphism in coding region) with a molecular weight of 14.471 or 14.185 kDa and a pI of 4.61 or 4.53 (FIG. 1A). As predicated by the PSORT II program (University of Tokyo, Japan) (psoll.ims.u-tolkyo.ac.jp), this peptide is localized in the nucleus and has a leucine zipper motif in the C terminus. The predicted chicken THRSPα peptide (FIG. 1A) has a low similarity (29% identities; 46% positives) to the human THRSP aa sequence (Grillasca et al., 1997) and to a gastrulation specific protein, G12 (33% identities; 45% positives) found in zebrafish (Conway, 1995). When a BlastX search of 1630 chicken protein sequences, derived from complete open reading frames in the UD CAP3 chicken EST assemblies, was made against the non-redundant human protein set in GenBank, the similarity of THRSPα was among the weakest 2%.

The chicken THRSPβ (UD CAP3 Contig_8452.2) was identified by searching the chicken UD CAP3 contig database, using chicken THRSPα cDNA as an "electronic" probe. The THRSPβ in silico cDNA was assembled from eight ESTs found in the BBSRC collection (adult liver, 5 ESTs; adult adipose tissue, 2 ESTs; adult heart, 1 EST); it is 670 bp long with a typical poly(A) signal sequence. The THRSPβ cDNA is almost identical to THRSPα isoform in the first 230 nt at the 5'-end, which encodes a nearly identical N-terminus. The overall similarity of the chicken THRSPα and THRSPβ paralogs is 70% identical and 79% positive (FIG. 1B). The THRSPβ cDNA is extremely GC-rich in the 3'-end, which makes it a difficult target for cloning and PCR amplification. Similar to the THRSPα isoform, the predicted THRSPβ protein is acidic (pI 5.1 or 4.96) with a molecular weight of 14.470 or 14.656 kDa and a leucine zipper motif in the C-terminus.

2.2 Sequence Alignment and Structural Analysis of Spot 14 Protein Family

A protein database search has revealed that THRSP family has three structurally related members in chickens and zebrafish, whereas mammals (i.e., human, mouse or rat) have only two members. A sequence comparison shows the structural similarity among Spot 14 (THRSP), the zebrafish gastrulation-specific protein (G12), and the hypothetical human protein (STRAIT11499) for chicken, human, mouse, rat and zebrafish (FIG. 2). The Spot 14 protein family shares three conserved domains: a highly hydrophobic aa sequence (PSLLRDV) near N-terminus, a second hydrophobic region in the middle and the leucine zipper motif in the carboxyl terminus.

A phylogenetic analysis shows that a common ancestor of birds, fishes and mammals could have two genes that encode structurally related proteins (FIG. 3). The THRSP protein is found in chickens, humans, rodents and zebrafish (zTC192887). The second member of the THRSP protein family found among these animals is the hypothetical [human] STRAIT11499 proteins, which includes the two zebrafish orthologs (G12 and zTC194742). The THRSP gene is duplicated in chickens, whereas the gastrulation-specific G12 gene is duplicated in zebrafish. The zG12 and zTC194742-derived proteins found in zebrafish are similar in aa sequence (57% identity; 73% positive). In contrast, the zebrafish THRSP protein (derived from zTC192887) is different from both G12 (40% identical; 58% positive) and zTC194742 (47% identical; 60% positive) proteins.

2.3. Genomic Organization

To gain some insight into the genomic organization of the two chicken genes, Southern blot analysis was performed using a probe that hybridizes to both genes, although the hybridization signal was stronger with .alpha. isoform (FIG. 4A). Genomic sequence of 15 kb that includes the THRSP.alpha. gene and its flanking regions was assembled from raw chicken genome trace files in GenBank (ncbi.nih.gov/Traces/trace.cgi). Alignment of THRSP.alpha. cDNA sequence with chicken genomic sequence shows that this gene contains two exons and one intron (FIGS. 1A and 4C). Similar to the human gene, the first exon encodes the entire cTHRSP protein, while exon 2 represents the 3'-UTR. Analysis of about 800 bp in the 5'-flanking region of the THRSP.alpha. gene shows a TATA box that is 39 bp upstream of the transcription start site (FIG. 4C).

Figure 5:
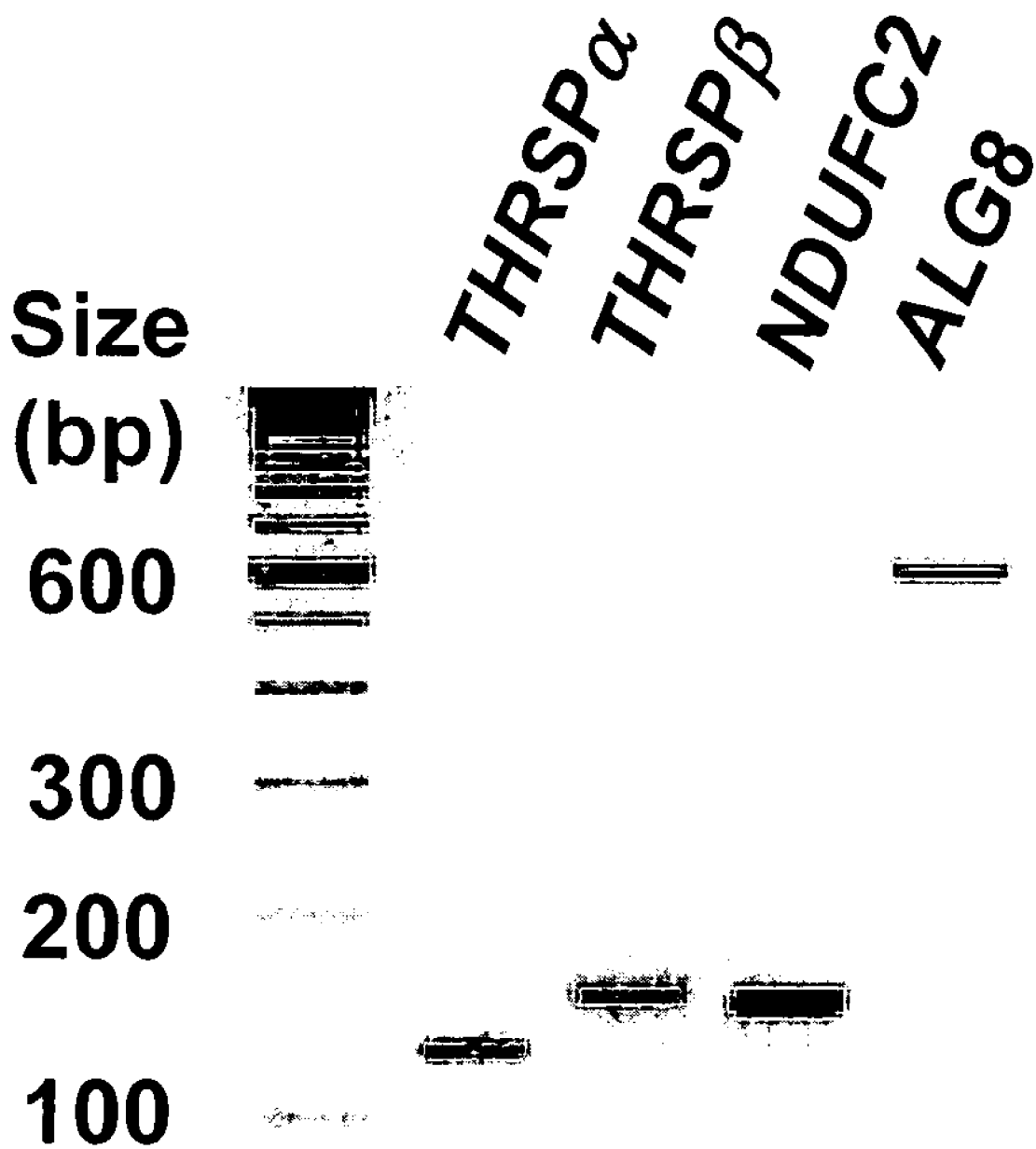
FIG. 5 shows the identification of a synteny group in chicken genomic DNA that includes THRSP and two flanking genes [NADH dehydrogenase (NDUFC2) and glucosyltransferase (ALG8)]. This presence of this synteny group in chicken genomic DNA was confirmed by PCR amplification of all four genes in two THRSP-positive BAC clones (65J23 and 94A1) that were identified earlier by Carre et al (2001), where only PCR products amplified from chicken BAC clone # 65J23 are shown. This synteny group is conserved in chickens [cChr1q41-44], humans [11q13.5], rat [rChr1q32-33] and mouse [mChr7D3-E1].

Genes in the vicinity were searched using the strategy described in section 2.1. Genomic sequence (ssi42g12.b1, GenBank GI no. 253911732) for THRSPβ was identified in one end of a genomic clone. The other end of the same genomic clone (ssi42g12.g1, GenBank GI no. 253911843) contained the THRSPα gene. Therefore, the chicken THRSP paralogs are closely linked, probably within a few kb, (see FIG. 4B) and are transcribed from the same direction. Coding sequences for chicken orthologs of human hypothetical protein (MGC2376; GenBank accession no. XP_133614), NADH dehydrogenase (NDUFC2) and were also found to flank Spot 14 (THRSPα) by in silico chromosomal walking. PCR analysis of two previously identified (Carre et al., 2001) THRSP-positive BAC clones (65J23 and 94A1) demonstrates the presence of THRSPα-β, NDUFC2 and glucosyltransferase (ALG8) from this synteny group in chicken genomic DNA (FIG. 5).

2.4. Expression of THRSP Genes

The expression of the chicken THRSP genes was examined by qRT-PCR using two primers (32F/93R) that are common to both THRSPα and THRSPβ (Table 1; FIGS. 1A and 1B). Among 11 tissues examined, liver had the highest expression level of THRSP mRNA, with fat, thymus and ovary expressing lower amounts (FIG. 6A). Thus, the THRSP genes appear to be predominantly expressed in lipogenic tissue in the chicken. Direct measurement of THRSPβ was not possible by TaqMan analysis (qRT-PCR) because the unique region in THRSPβ cDNA is very GC-rich. Therefore, an indirect method was used to examine THRSPβ expression in liver and fat tissue (FIG. 6B). First, we obtained the total THRSP mRNA level by using 32F/93R primer pairs; then, the THRSPα mRNA level was determined using the specific DeletionF/DeletionR primer set. The relative abundance of THRSPβ was calculated from the difference between total THRSP and specific THRSPα mRNA levels (FIGS. 6B, -C and -D). The relative abundance of THRSPα and THRSPβ was examined in liver and abdominal fat of five-week-old broiler chickens (4), where the abundance of THRSPα was 2- to 3-times greater than that of THRSPβ, respectively (FIG. 6B). Previously, a dramatic increase in chicken total THRSP mRNA levels in liver of 1 day old chicks was found when compared to late embryos (e16, e18 and e20) (Cogburn et al., 2003b). Therefore, we examined whether the expression of THRSPα and THRSPβ was differentially regulated during this period. A dramatic increase of 13- to 20-fold was detected in THRSPα and THRSPβ (FIG. 6C) mRNA levels (respectively) at 1 day post-hatching. Since the expression of THRSP responds rapidly to nutritional factors, we also examined whether prolonged fasting and re-feeding (Beccavin et al., 2001) would differentially regulate expression of the hepatic THRSP paralogs. Both THRSPα and THRSPβ mRNA levels were down-regulated after a 48 hr fast and up-regulated at 4 hr after re-feeding (FIG. 6D), although the re-feeding response of THRSPβ was slightly higher (8-fold increase) than that of THRSPα (5-fold increase). Therefore, the transcription of THRSPα and THRSPβ appears to respond similarly to developmental and nutritional factors.

Figure 7:
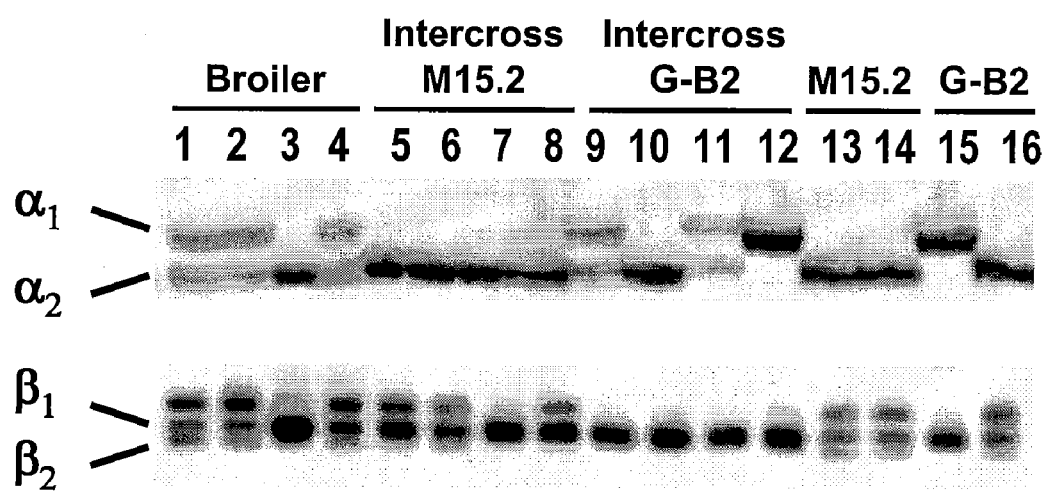
FIG. 7 shows evidence of polymorphisms in THRSPα and THRSPβ genes in a group of stock chickens from the Iowa Growth and Composition Resource Population (IGCRP). Genomic DNA (40 ng) from 16 chickens of mixed sexes, randomly chosen from contemporary pure founder lines, was amplified by PCR with specific primers for either THRSPα (DeletionF/DeletionR) or THRSPβ (ParalogF/ParalogR). The PCR products for THRSPα (Allele α1=136 bp; Allele α2=127 bp) were labeled with $^{32}$P-dCTP, separated in native polyacrylamide gel (8%), exposed to a phosphorimager screen overnight and visualized with a PhosphorImager (Storm 840, Molecular Dynamics). The PCR products for THRSPβ (Alleleβ1 =151 bp; Allele β2=145 bp) were amplified with ThermalAce (Invitrogen) and separated in a 3% agarose gel.

2.5. THRSPα and THRSPβ Polymorphisms (Haplotypes) and their Association with Abdominal Fat Traits Both THRSP.alpha. and THRSP.beta. genes are polymorphic which involves a number of iterations of short repeats [9 bp (ATAGATGGC) in THRSP.alpha. and 6 bp (GCCGAC) in THRSP.beta.] located in the middle of protein coding region near leucine zipper motif. These polymorphisms result in the insertion or deletion of three aa in THRSP.alpha. and two aa in THRSP.beta. protein. These polymorphisms represent a haplotype which is a set of linked alleles from linked genes on one chromosome. The F.sub.2 generation from the broiler.times.Leghorn cross represented in the IGCRP (Deeb and Lamont, 2002) were genotyped for THRSP.alpha. and THRSP.beta. alleles or haplotypes (FIG. 7; Table 2) to determine if the THRSP haplotypes are associated with deposition of abdominal fat in chickens from this resource population. In FIG. 7 and Table 2, allele .alpha.1 represents the THRSP a insertion. Allele .alpha.2 represents the THRSP a deletion. Allele .beta.p1 represents the THRSP .beta. insertion. Allele .beta..sub.2 represents the THRSP .beta. deletion.

The THRSP α1β1/α2β2 genotype was associated with the lowest abdominal fat content [Fat (g) and % Fat] in the broiler.times.Leghorn cross (Table 2). In contrast, the greatest amount of abdominal fat [Fat (g) and % Fat (% BW) traits] was associated with the THRSP α1β2/α1β2 genotype. This represents a difference of about 7.5 g of body fat between the two genotypes. There are four possible haplotypes, α1β1, α1β2, α2β1 and α2β2. In the present example, only three of the haplotypes were found (α1β1, α1β2, and α2β2). The leanest haplotype in this example was α1β2, and the fattest α2β2. We predict from these data that the |leanest haplotype |would be α2β1, although it was not found in the present population.

3. Discussion

The discovery of duplicated, but distinct, Spot 14 (THRSPα and THRSPβ) genes and the insertion/deletion polymorphisms in THRSPα and THRSPβ that is associated with abdominal fat traits are described. A search of our CAP3 database of chicken EST assemblies has also revealed a third structurally-related member of the THRSP protein family in chickens (cSTRAIT11499). A search for orthologs of this protein family in human, mouse, rat and zebrafish, where extensive EST data are available, has revealed three members of the THRSP protein family in chickens (THRSPα, THRSPβ and cSTRAIT11499) and zebrafish [zTHRSP (zTC192887), zG12 and zTC194742]. In contrast, there are only two family members found in mammals (THRSP and STRAIT11499). All members of this protein family have three conserved domains which could be of functional importance (FIG. 2). Another chicken EST (a singlet) found in the BBSRC database (GenBank accession no. BU440998) has an exceptionally high homology (99% nucleotide sequence identity) to bovine THRSP; however, this probably represents a contaminating bovine cDNA sequence.

A synteny group, containing an ortholog of MGC2376, NADH dehydrogenase (NDUFC2) and glucosyltransferase (ALG8), flanks the chicken THRSPα and THRSPβ genes and is highly conserved among chickens, rats, mice and humans, where they are located on cChr1q41-44, rChr1q32-33, mChr7D3-E1 and hChr11q13.5, respectively. Our study clearly shows that one of the THRSP genes appears after the divergence of mammals and birds. This finding suggests that a chromosomal duplication event has occurred in the chicken. Gene duplication is a common process in genome evolution (Tatusov et al., 1997), where each copy of the duplicated genes acquires different mutations that could lead to altered function. One copy of a duplicated gene usually shows a faster rate of evolution (Zhang et al., 2003). THRSPβ is more similar in aa sequence to mammalian THRSP. However, chicken THRSPβ has an unusually high GC content, a feature that is not found in either human or mouse orthologs. We have shown that expression of the THRSP paralogs is coordinately regulated in liver and fat, during post-hatching development and by re-feeding. It is interesting to note that the flanking NDUFC2 gene in chicken is also highly polymorphic. Alignment of 22 ESTs and chicken genomic trace sequence reveals two alternatively-spliced isoforms and two polymorphic sites in chicken NDUFC2. One site is located in the 5'-UTR and involves a gcc repeat, whereas the other polymorphic site is located in the 3'-UTR and involves four bp (ataa). Therefore, this chromosomal region in the chicken appears to be a hot spot for genomic reorganization.

Expression of the murine THRSP has been extensively studied in liver and adipose tissue, where nutritional and hormonal factors intricately regulate its expression (Clarke et al., 1990; Jump et al., 1994; Liu and Towle, 1994). Enhanced long-chain fatty acid synthesis occurs in lipogenic breast cancer, where THRSP is necessary for tumor growth. Therefore, amplification of the THRSP gene is a prognosticator of lipogenic breast cancer in humans (Moncur et al., 1998). In the present study, we have demonstrated the association of the THRSPα and THRSPβ polymorphisms with abdominal fat traits in a broiler×Leghorn cross. There is a clear association of the THRSPα and THRSPβ haplotypes with fat traits. The insertion/deletion polymorphisms in THRSPα and explains about 14% of the variation in abdominal fat, which correlates well with the estimate of about 21 polygenes that control expression of the % Fat trait in this population (Deeb and Lamont, 2002). It is particularly interesting that the insertion/deletion polymorphisms in the THRSPα and THRSPβ paralogs involve aspartic acid near the leucine zipper motif, which is critical for homodimerization of THRSP and subsequent transcriptional control of lipogenic enzymes (Cunningham et al., 1997). This could add additional complexity to dimerization of this acidic transcriptional activator in chickens. In some chickens, there are four different isoforms of THRSP that could form different dimmer combinations. If these isoforms act differently in controlling fat deposition, it could be much more complicated to determine the effect of each individual allele.

Our initial transcriptional profiling studies have shown that the expression of THRSP in liver is up-regulated by metabolically-active $T_3$, post-hatching development and re-feeding after a prolonged period of fasting. In chickens, this thyroid hormone-regulated putative transcription factor (THRSP) appears to play a key role in regulating the expression of six enzymes in the lipogenic pathway (see FIG. 4 in Cogburn et al., 2003b). As a homodimer, THRSP interacts with nuclear receptors (i.e., COUP-TF1) in the transcriptional control of lipogenic enzymes (Cunningham et al., 1997; Cunningham et al., 1998; Compe et al., 2001). Furthermore, the mammalian THRSP promoter contains multiple response elements that respond to thyroid hormone (TRE) (Liu and Towle, 1994), carbohydrates (ChoRE) (Koo and Towle, 2000) and sterols (SRE, sterol response element), particularly SREBP-1c (Jump et al., 2001). These multiple response elements exert THRSP's control over the expression of key lipogenic, glycolytic and gluconeogenic enzymes in a tissue-specific and fuel-dependent manner (Brown et al., 1997). In chickens, the expression of THRSP mRNA increases dramatically in the liver of newly-hatched chicks as they begin to synthesize and deposit abdominal fat. It has been consistently found that THRSP responds to metabolic perturbations and it is found in clusters of functionally-related genes (i.e., enzymes and transcription factors) that control metabolism and fat deposition in the chicken (Cogburn et al., 2003a; Cogburn et al., 2003b).

4. Conclusions

Duplicated paralogs of Spot 14 in the chicken, THRSPα and THRSPβ were identified by sequence analysis of contigs assembled from our chicken EST collection and those in public databases (>309,000 ESTs). A computational analysis of THRSP proteins has reveal three highly-conserved domains in two structurally-related proteins from the THRSP family (THRSP and STRAIT11499, a hypothetical human protein) across a number of vertebrates (chicken, zebrafish, rat, mouse and human). Transcription of THRSPα and THRSPβ mRNA in lipogenic tissues appears to be controlled by developmental, hormonal and nutritional factors. Polymorphic alleles involving tandem repeats (of either 9 or 6 bp) were found in the putative protein coding region of the chicken THRSPα (a 9 bp indel) and THRSPβ (a 6 bp indel) genes. Our study shows that the THRSPα and THRSPβ loci are associated with abdominal fat traits in a broiler×Leghorn resource population. Furthermore, assembly of THRSP-positive chicken genomic sequences has revealed a synteny group of THRSP and its flanking genes [NADH dehydrogenase (NDUFC2) and glucosyltransferase (ALG8)] that is highly conserved in chickens, humans, mice and rats. The chicken THRSP genes are located on Chr1q41-44 near QTL for fatness. These observations support a role of THRSP in control of lipogenesis and expression of abdominal fat traits in the domestic chicken.

TABLE 1

Quantitative RT-PCR (TaqMan) and PCR Primers

| Gene | | Primer Sequence | SEQ ID NO: | Amplicon Size (bp) |
|---|---|---|---|---|
| 18S RNA* | Forward | GTGCATTTATCAGACCAAAACCAA | 14 | 76 |
| | Reverse | GCGATCGGCTCGAGGTTA | 15 | |
| THRSPa* | DeletionF | GCCTCCGTCACCGATCAG | 16 | 127 or 136 |
| | DeletionR | CGGTCAGAACCTGCTGCAA | 17 | |
| THRSPB | ParalogF | GCGTCCTTCACCGAGCG | 18 | 145 or 151 |
| | ParalogR | TGGCTGAGGATCTGCTGCAG | 19 | |
| NDUFC2 | 465F | CGTGTGGATGGCAAGATGTT | 20 | 151 |
| | 615R | CAACTCCAGGCTTGCTGCAT | 21 | |
| ALG8 | 1053F | GCCTTGTTGTTTGTGCGTTG | 22 | 460 |
| | 1203R | AAATGCCCTGTGGTTGTCAGA | 23 | |
| Total THRSP* | 32F | TTCTCGGCCACGCAGAAG | 24 | 71 |
| | 93R | AAGACCCCTCGCAGCAGG | 25 | |

*These primer sets were used in TaqMan real-time qRT-PCR analysis.

TABLE 2

Association of chicken THRSPα and THRSPβ alleles (haplotypes) with fat traits in the Iowa Growth and Composition Resource Population (IGCRP)

| Genotype | Number of Birds | Abdominal Fat Weight (g) | Fat (% BW) |
|---|---|---|---|
| α1β1/α2β2 | 28 | 47.43 ± 2.92$^a$ | 2.88 ± 0.17$^a$ |
| α2β2/α2β2 | 43 | 52.11 ± 2.30$^{ab}$ | 3.27 ± 0.13$^{ab}$ |
| α1β2/α1β1 | 39 | 50.44 ± 2.58$^{ab}$ | 3.27 ± 0.15$^{ab}$ |
| α1β2/α2β2 | 156 | 50.97 ± 1.19$^{ab}$ | 3.23 ± 0.07$^{ab}$ |
| α1β2/α1β2 | 106 | 54.96 ± 2.30$^b$ | 3.45 ± 0.08$^b$ |

Note:
The traits used were abdominal fat weight (g) and abdominal fat expressed as a percent of body weight (% BW).
Values ± SEM that possess a different superscript letter are significantly ($P < 0.05$) different.

REFERENCES

Beccavin et al., 2001, Insulin-like growth factors and body growth in chickens divergently selected for high or low growth rate. J. Endocrinol. 168, 297-306.

Boardman et al., 2002, A comprehensive collection of chicken cDNAs. Curr. Biol. 12, 1965-1969.

Brown et al. 1997. "Spot 14" protein functions at the pretranslational level in the regulation of hepatic metabolism by thyroid hormone and glucose. J. Biol. Chem. 272, 2163-2166.

Carre et al. 2001. Development of 112 unique expressed sequence tags from chicken liver using an arbitrarily primed reverse transcriptase-polymerase chain reaction and single strand conformation gel purification method. Anim. Genet. 32, 289-297.

Clarke et al., 1990. Nutritional control of rat liver fatty acid synthase and S14 mRNA abundance. J. Nutr. 120, 218-224.

Cogburn et al., 2000. DNA microarray analysis of gene expression in the liver of broiler chickens divergently selected for growth rate. Poult. Sci. 79 (suppl. 1), 72.

Cogburn et al., 2003a. Expressed sequence tags, DNA chip technology and gene expression profiling. In: Muir, M. W. and Aggrey, S. E. (Eds.), Poultry Genetics, Breeding and Biotechnology. CABI Publishing, Wallingford, Oxon, UK, pp. 629-646.

Cogburn et al., 2003b. Systems-wide chicken DNA microarrays, gene expression profiling and discovery of functional genes. Poult. Sci. 82, 6378-6383.

Compe et al., 2001. Spot 14 protein interacts and co-operates with chicken ovalbumin upstream promoter-transcription factor 1 in the transcription of the L-type pyruvate kinase gene through a specificity protein 1 (Sp1) binding site. Biochem. J. 358, 175-183.

Conway, G., 1995. A novel gene expressed during zebrafish gastrulation identified by differential RNA display. Mech. Dev. 52, 383-391.

Cunningham et al., 1997. Spot 14 protein-protein interactions: evidence for both homo- and heterodimer formation in vivo. Endocrinology 138, 5184-5188.

Cunningham et al., 1998. "Spot 14" protein: a metabolic integrator in normal and neoplastic cells. Thyroid 8, 815-825.

Deeb, N., Lamont, S. J., 2002. Genetic architecture of growth and body composition in unique chicken populations. J. Hered. 93, 107-18.

Griffin et al., 1992. "Adipose tissue lipogenesis and fat deposition in leaner broiler chickens", J. Nutr. 122,363-368.

Grillasca et al., 1997. Cloning and initial characterization of human and mouse Spot 14 genes. FEBS Lett. 401, 38-42.

Huang, X., Madan, A., 1999. CAP3: A DNA sequence assembly program. Genome Res. 9, 868-877.

Ikeobi et al., 2002. Quantitative trait loci affecting fatness in the chicken. Anim. Genet. 33, 428-435.

Jump et al., 1984. Rapid effects of triuodothyronine on hepatic gene expression. Hybridization analysis of tissue-specific truiodothyronine regulation of mRNAS14. J. Biol. Chem. 259, 2789-2797.

Jump, D. B., Oppenheimer, J. H., 1985. High basal expression and 3,5,3'-triiodothyronine regulation of messenger ribonucleic acid S14 in lipogenic tissues. Endocrinology 117, 2259-2266.

Jump et al., 1993. Polyunsaturated fatty acids inhibit S14 gene transcription in rat liver and cultured hepatocytes. Proc. Natl. Acad. Sci. 90, 8454-8458.

Jump et al., 1994. Coordinate regulation of glycolytic and lipogenic gene expression by polyunsaturated fatty acids. J. Lipid Res. 35, 1076-1084.

Jump et al., 2001. Functional interaction between sterol regulatory element-binding protein-1c, nuclear factor Y, and 3,5,3'-triiodothyronine nuclear receptors. J. Biol. Chem. 276, 34419-34427.

Kinlaw et al., 1995. Direct evidence for a role of the "spot 14" protein in the regulation of lipid synthesis. J. Biol. Chem. 270, 16615-16618.

Koo, S. H., Towle, H. C., 2000. Glucose regulation of mouse S(14) gene expression in hepatocytes. Involvement of a novel transcription factor complex. J. Biol. Chem. 275, 5200-5207.

Lagarrigue et al., 2003. "An initial QTL scan for abdominal fatness and breast muscle weight in broiler chickens.", Plant & Animal Genome XI Conference, San Diego, Calif., 2003, pp. 595.

Leclerq et al., 1980. "Selecting broilers for low or high abdominal fat: initial observations" Br. Poul. Sci. 21, 107-113.

Legrand, P. and Hermier, D., 1992. "Hepatic D9 desaturation and plasma VLDL in genetically lean and fat chickens." Int. J. Obesity 16, 289-294.

Liaw, C. W., Towle, H. C., 1984. Characterization of a thyroid hormone-responsive gene from rat. J. Biol. Chem. 259, 7253-7260.

Liu, H. C., Towle, H. C., 1994. Functional synergism between multiple thyroid hormone response elements regulates hepatic expression of the rat S14 gene. Mol. Endocrinol. 8, 1021-1037.

Moncur et al., 1998. The "Spot 14" gene resides on the telomeric end of the 11q13 amplicon and is expressed in lipogenic breast cancers: implications for control of tumor metabolism. Proc. Natl. Acad. Sci. 95, 6989-6994.

O'Hea, E. K. and Leveille, G. A., 1968. "Lipogenesis in isolated adipose tissue of the domestic chick (*Gallus domesticus*)" Comp. Biochem. Physiol. 26, 111-120.

Sall, J., Lehman, A., 1996. JMP Start Statistics: A guide to statistical and data analysis using JMP and JMP IN software. Duxbury Press, Wadsworth Publishing Company, Belmont, Calif.

Seelig et al., 1981. Thyroid hormone attenuates and augments hepatic gene expression at a pretranslational level. Proc. Natl. Acad. Sci. 78, 4733-4737.

Tatusov et al., 1997. A genomic perspective on protein families. Science 278, 631-637.

Whitehead, C. C., Griffin, H. D., 1984. "Development of divergent lines of lean and fat broilers using plasma very low density lipoprotein concentration as selection criterion: the first three generations". Br. Poult. Sci. 25, 573-582.

Zhang et al., 2003. Different evolutionary patterns between young duplicate genes in the human genome. Genome Biol. 4, R56.

Zhou, H., Lamont, S. J., 1999. Genetic characterization of biodiversity in highly inbred chicken lines by microsatellite markers. Anim. Genet. 30, 256-264.

Zhu et al., 2001. Spot 14 gene deletion increases hepatic de novo lipogenesis. Endocrinology 142, 4363-4370.

We claim:

1. A method of screening a chicken to determine that the chicken is more likely to have a lean phenotype or a fat phenotype, the method comprising:
   a) obtaining a biological sample from the chicken, wherein the biological sample comprises nucleic acids from the chicken; and
   b) detecting in the nucleic acids the presence of a THRSP α1β1/α2β2 genotype or a THRSP α1β2/α1β2 genotype, wherein the THRSP α1 allele is identified by detecting the presence of SEQ ID NO: 1 in the nucleic acids, the THRSP α2 allele is identified by detecting the deletion of nucleotides 261-269 from SEQ ID NO: 1 in the nucleic acids, the THRSP β1 allele is identified by detecting SEQ ID NO: 3 in the nucleic acids, and the THRSP β2 allele is identified by detecting the deletion of nucleotides 228-233 from SEQ ID NO: 3 in the nucleic acids; and
   c) correlating the presence of the α1β1/α2β2 genotype with an increased likelihood of the chicken having a lean phenotype, or correlating the presence of the α1β2/α1β2 genotype with an increased likelihood of the chicken having a fat phenotype, wherein a chicken with a lean phenotype has less abdominal fat weight and a lower percentage of body weight that is fat, and a chicken with a fat phenotype has more abdominal fat weight and a higher percentage of body weight that is fat.

2. The method of claim 1, wherein step b) further comprises amplifying at least one portion of the genetic material with a primer pair capable of detecting a polymorphism within SEQ ID NO: 1 or SEQ ID NO: 3.

3. The method of claim 2 wherein the primer pair consists of SEQ ID NOs:16 and 17 or SEQ ID NOs:18 and 19.

4. The method of claim 3, wherein the primer pair consists of SEQ ID NOs: 16 and 17.

5. The method of claim 3, wherein the primer pair consists of SEQ ID NOs: 18 and 19.

* * * * *